United States Patent [19]

Murugesan

[11] Patent Number: 5,612,359

[45] Date of Patent: Mar. 18, 1997

[54] SUBSTITUTED BIPHENYL ISOXAZOLE SULFONAMIDES

[75] Inventor: Natesan Murugesan, Lawrenceville, N.J.

[73] Assignee: Bristol-Myers Squibb Company, Princeton, N.J.

[21] Appl. No.: 487,358

[22] Filed: Jun. 7, 1995

Related U.S. Application Data

[63] Continuation-in-part of Ser. No. 368,285, Jan. 4, 1995, abandoned, which is a continuation-in-part of Ser. No. 297,187, Aug. 26, 1994, abandoned.

[51] Int. Cl.$^6$ .................... A01K 31/465; C07D 417/12
[52] U.S. Cl. .................... 514/365; 514/374; 514/380; 548/205; 548/236; 548/238; 548/245
[58] Field of Search .................... 548/238, 205, 548/245, 236; 514/365, 374, 500

[56] References Cited

U.S. PATENT DOCUMENTS

| | | | |
|---|---|---|---|
| 2,888,455 | 5/1959 | Kano et al. | |
| 4,415,496 | 11/1983 | Harris et al. | |
| 4,661,479 | 4/1987 | Wyvratt, Jr. et al. | |
| 5,236,928 | 8/1993 | Chakravarty et al. | 514/275 |
| 5,270,313 | 12/1993 | Burri et al. | 514/252 |
| 5,292,740 | 3/1994 | Burri et al. | 514/256 |
| 5,378,715 | 1/1995 | Stein et al. | |
| 5,464,853 | 11/1995 | Chan et al. | 514/378 |
| 5,514,691 | 5/1996 | Chan et al. | 514/312 |
| 5,514,696 | 5/1996 | Murugesan et al. | 514/380 |

FOREIGN PATENT DOCUMENTS

| | | |
|---|---|---|
| 29589/92 | 5/1993 | Australia. |
| 34011/93 | 9/1993 | Australia. |
| 67357/94 | 1/1995 | Australia. |
| 76072 | 4/1983 | European Pat. Off. |
| 194548 | 9/1986 | European Pat. Off. |
| 404525 | 12/1990 | European Pat. Off. |
| 443983 | 8/1991 | European Pat. Off. |
| 510526 | 10/1992 | European Pat. Off. |
| 526708 | 2/1993 | European Pat. Off. |
| 558258 | 9/1993 | European Pat. Off. |
| 569193 | 11/1993 | European Pat. Off. |
| 601386 | 6/1994 | European Pat. Off. |
| 617001 | 9/1994 | European Pat. Off. |
| 626174 | 11/1994 | European Pat. Off. |
| 633259 | 1/1995 | European Pat. Off. |
| 634175 | 1/1995 | European Pat. Off. |
| 640596 | 3/1995 | European Pat. Off. |
| 1059459 | 6/1959 | Germany. |
| 0364506 | 11/1962 | Switzerland. |
| 804036 | 11/1958 | United Kingdom. |
| 0897440 | 5/1962 | United Kingdom. |
| 1473433 | 5/1977 | United Kingdom. |
| 2228933 | 9/1990 | United Kingdom. |
| 91/15479 | 10/1991 | WIPO. |
| 93/08799 | 5/1993 | WIPO. |
| 93/23404 | 11/1993 | WIPO. |
| 94/27979 | 12/1994 | WIPO. |

OTHER PUBLICATIONS

Chan et al., "Identification of a New Class of ET$_A$ Selective Endothelin Antagonists by Pharmacophore Directed Screening", Biochemical and Biophysical Research Communications, vol. 201, No. 1, May 30, 1994, pp. 228–234.

Stein et al., "The Discovery of Sulfonamide Endothelin Antagonists and the Development of the Orally Active ET$_A$ Antagonist 5-(Dimethylamino)-N-(3, 4-dimethyl-5-isoxazolyl)-1-naphthalenesulfonamide", J. Med. Chem., vol. 37, No. 3, Feb. 4, 1994, pp. 329–331.

S. Norio et l., Chemical Abstracts, vol. 70, No. 19, (1969), 87639g.

T. Saito, Chemical Abstracts, vol. 73, No. 23 (1970), 120511w.

Derwent Abstract No. 88–289069/41 Feb. 27, 1987.

Derwent Abstract No. 88–195835/28 Nov. 26, 1986.

(List continued on next page.)

*Primary Examiner*—Robert Gerstl
*Attorney, Agent, or Firm*—Suzanne E. Babajko

[57] ABSTRACT

Compounds of the formula

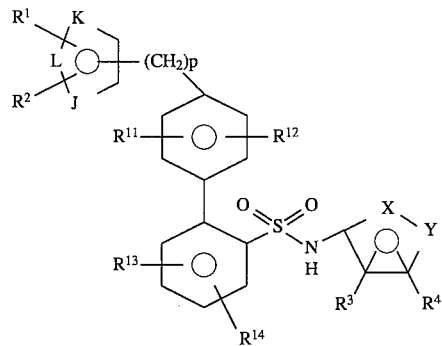

inhibit the activity of endothelin. The symbols are defined as follows:

$R^1$, $R^2$, $R^3$ and $R^4$ are each directly bonded to a ring carbon and are each independently (a) hydrogen;
(b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with $Z^1$, $Z^2$ and $Z^3$;
(c) halo;
(d) hydroxyl;
(e) cyano;
(f) nitro;
(g) —C(O)H or —C(O)$R^5$;
(h) —CO$_2$H or —CO$_2R^5$;
(i) —$Z^4$—NR$^6$R$^7$;
—$Z^4$—N(R$^{10}$)—$Z^5$—NR$^8$R$^9$; or
(k) $R^3$ and $R^4$ together may also be alkylene or alkenylene, either of which may be substituted with $Z^1$, $Z^2$ and $z^3$, completing a 4- to 8-membered saturated, unsaturated or aromatic ring together with the carbon atoms to which they are attached; and the remaining symbols are as defined in the specification.

73 Claims, No Drawings

OTHER PUBLICATIONS

Derwent Abstract No. 88–061295/09 Jul. 9, 1986.
Derwent Abstract No. 87–152485/22 Oct. 11, 1985.
Derwent Abstract No. 62299 E/30 Dec. 11, 1980.
Derwent Abstract No. 40927 D/23 Sep. 11, 1979.
Derwent Abstract No. 91–254550/35 Feb. 19, 1990.
Derwent Abstract No. 86–246709/38 Nov. 27, 1985.
Derwent Abstract No. 35012 K/15 Sep. 24, 1981.
Allen et al., "Preparation . . . antagonists", CA116(11):106284Z, p. 778, 1992.
R.D. Desai et al., Chemical Abstracts, vol. 71, No. 11, (1969) 49825c.

R.D. Desai et al., Chemical Abstracts, vol. 71, No. 3, (1969) 12872q.

P. G. Ferrini et al., Angew. Chem. Internat. Edit., vol. 2, No. 2 (1963) p. 99.

A. M. van Leusen, et al., "Synthesis . . . Compounds" J. Org. Chem., vol. 41, 4, (1976), pp. 69–71.

W. J. Hammar et al., J. Heterocyclic Chem., vol. 18, (1981) pp. 885–888.

A. M. van Leusen et al., Tetrahedron Letters, No. 23, (1972), pp. 2369–237.

SUBSTITUTED BIPHENYL ISOXAZOLE SULFONAMIDES

This application is a continuation-in-part of application serial number 08/368,285 filed on Jan. 4, 1995 now abandoned, which in turn is a continuation-in-part of application Ser. No. 08/297,187 filed on Aug. 26, 1994 now abandoned. The entire contents of both of these applications are hereby incorporated by reference.

FIELD OF THE INVENTION

This invention relates to endothelin antagonists useful, inter alia, for treatment of hypertension.

BRIEF DESCRIPTION OF THE INVENTION

Compounds of the formula I

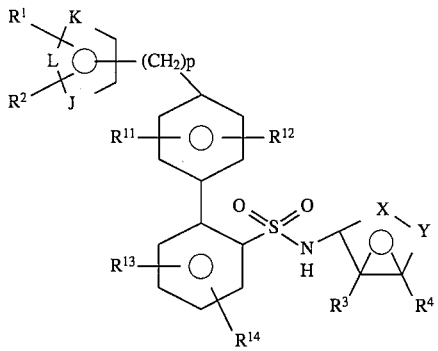

its enantiomers and diastereomers, and pharmaceutically acceptable salts thereof are endothelin receptor antagonists useful, inter alia, as antihypertensive agents. Throughout this specification, the above symbols are defined as follows:

one of X and Y is N and the other is O;

$R^1$, $R^2$, $R^3$ and $R^4$ are each directly bonded to a ring carbon and are each independently
   (a) hydrogen;
   (b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with $Z^1$, $Z^2$ and $z3$;
   (c) halo;
   (d) hydroxyl;
   (e) cyano;
   (f) nitro;
   (g) —C(O)H or —C(O)$R^5$;
   (h) —CO$_2$H or —CO$_2R^5$;
   (i) —$Z^4$—NR$^6$R$^7$;
   (j) —$Z^4$—N(R$^{10}$)—$Z^5$—NR$^8$R$^9$; or
   (k) $R^3$ and $R^4$ together may also be alkylene or alkenylene, either of which may be substituted with $Z^1$, $Z^2$ and $Z^3$, completing a 4- to 8-membered saturated, unsaturated or aromatic ring together with the carbon atoms to which they are attached;

$R^5$ is alkyl, alkenyl, alkynyl, cycloalkyl, cycloalkylalkyl, cycloalkenyl, cycloalkenylalkyl, aryl or aralkyl, any of which may be substituted with $Z^1$, $Z^2$ and $Z^3$;

$R^6$, $R^7$, $R^8$, $R^9$ and $R^{10}$ are each independently
   (a) hydrogen; or
   (b) alkyl, cycloalkyl, cycloalkylalkyl, cycloalkenylalkyl, aryl or aralkyl, any of which may be substituted with $Z^1$, $Z^2$ and $Z^3$; or $R^6$ and $R^7$ together may be alkylene or alkenylene, either of which may be substituted with $Z^1$, $Z^2$ and $Z^3$, completing a 3- to 8-membered saturated or unsaturated ring together with the nitrogen atom to which they are attached; or any two of $R^8$, $R^9$ and $R^{10}$ together are alkylene or alkenylene, either of which may be substituted with $Z^1$, $Z^2$ and $Z^3$, completing a 3- to 8-membered saturated or unsaturated ring together with the atoms to which they are attached;

$R^{11}$, $R^{12}$, $R^{13}$ and $R^{14}$ are each independently
   (a) hydrogen;
   (b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with $Z^1$, $Z^2$ and $Z^3$,
   (c) halo;
   (d) hydroxyl;
   (e) cyano;
   (f) nitro;
   (g) —C(O)H or —C(O)$R^5$;
   (h) —CO$_2$H or —CO$_2R^5$;
   (i) —SH, —S(O)$_n$R$^5$, —S(O)$_m$—OH, —S(O)$_m$—OR$^5$, —O—S(O)m—OR$^5$, —O—S(O)$_m$OH or —O—S(O)$_m$—OR$^5$;
   (j) —$Z^4$—NR$^6$R$^7$; or
   (k) —$Z^4$—N(R$^{10}$)—$Z^5$—NR$^8$R$^9$;

$Z^1$, $Z^2$ and $Z^3$ are each independently
   (a) hydrogen;
   (b) halo;
   (c) hydroxy;
   (d) alkyl;
   (e) alkenyl;
   (f) aralkyl;
   (g) alkoxy;
   (h) aryloxy;
   (i) aralkoxy;
   (j) —SH, —S(O)$_n$Z$^6$, —S(O)$_m$—OH, —S(O)$_m$—OZ$^6$, —O—S(O)$_m$—Z$^6$, —O—S(O)$_m$OH or —O—S(O)$_m$—OZ$^6$;
   (k) oxo;
   (l) nitro;
   (m) cyano;
   (n) —C(O)H or —C(O)Z$^6$;
   (o) —CO$_2$H or —CO$_2$Z$^6$;
   (p) —$Z^4$—NZ$^7$Z$^8$;
   (q) —$Z^4$—N(Z$^{11}$)—$Z^5$—H;
   (r) —$Z^4$—N(Z$^{11}$)—$Z^5$—Z$^6$; or
   (s) —$Z^4$—N(Z$^{11}$)—$Z^5$-NZ$^7$Z$^8$;

$Z^4$ and $Z^5$ are each independently
   (a) a single bond;
   (b) —$Z^9$—S(O)$_n$—Z$^{10}$—;
   (c) —$Z^9$—C(O)—Z$^{10}$—;
   (d) —$Z^9$—C(S)—Z$^{10}$—;
   (e) —$Z^9$—O—Z$^{10}$—;
   (f) —$Z^9$—S—Z$^{10}$—;
   (g) —$Z^9$—O—C(O)—Z$^{10}$—; or
   (h) —$Z^9$—C(O)—O—Z$^{10}$—;

$Z^6$ is alkyl, alkenyl, alkynyl, cycloalkyl, cycloalkylalkyl, cycloalkenyl, cycloalkenylalkyl, aryl or aralkyl;

$Z^7$ and $Z^8$ are each independently hydrogen, alkyl, cycloalkyl, cycloalkylalkyl, cycloalkenylalkyl, aryl or aralkyl, or $Z^7$ and $Z^8$ together are alkylene or alkenylene, completing a 3- to 8-membered saturated or unsaturated ring together with the nitrogen atom to which they are attached;

$Z^9$ and $Z^{10}$ are each independently a single bond, alkylene, alkenylene or alkynylene;

$Z^{11}$ is (a) hydrogen; or (b) alkyl, cycloalkyl, cycloalkylalkyl, cycloalkenylalkyl, aryl or aralkyl;

or any two of $Z^7$, $Z^8$ and $Z^{11}$ together are alkylene or alkenylene, completing a 3- to 8-membered saturated or unsaturated ring together with the atoms to which they are attached;

J is O, S, N or $NR^{15}$;

K and L are N or C, provided that at least one of K or L is C;

$R^{15}$ is hydrogen, alkyl, hydroxyethoxy methyl or methoxyethoxy methyl;

each m is independently 1 or 2;

each n is independently 0, 1 or 2; and p is 0 or an integer from 1 to 2.

For compound I, it is preferred that:

$R^1$ and $R^2$ are each independently hydrogen, alkyl, alkoxy, aryl, hydroxyalkyl, $-CO_2R^5$ or $-Z^4-NR^6R^7$;

$R^3$ and $R^4$ are each independently alkyl; and $R^{11}$ and $R^{12}$ are each independently hydrogen, hydroxy, amino or substituted lower alkyl.

Most preferred compounds are those wherein:

$R^1$ and $R^2$ are each independently lower alkyl or hydrogen;

$R^3$ and $R^4$ are each independently lower alkyl, especially methyl; and $R^{11}$ and $R^{12}$ are each independently hydrogen, hydroxy or substituted lower alkyl.

DETAILED DESCRIPTION OF THE INVENTION

Listed below are definitions of terms used in this specification. These definitions apply to the terms as used throughout this specification, individually or as part of another group, unless otherwise limited in specific instances.

The term "alkyl" or "alk-" refers to straight or branched chain hydrocarbon groups having 1 to 10 carbon atoms, preferably 1 to 7 carbon atoms. The expression "lower alkyl" refers to alkyl groups of 1 to 4 carbon atoms.

The term "alkoxy" refers to alkyl-O—.

The term "aryl" or "ar-" refers to phenyl, naphthyl and biphenyl.

The term "alkenyl" refers to straight or branched chain hydrocarbon groups of 2 to 10 carbon atoms having at least one double bond. Groups of two to four carbon atoms are preferred.

The term "alkynyl" refers to straight or branched chain groups of 2 to 10 carbon atoms having at least one triple bond. Groups of two to four carbon atoms are preferred.

The term "alkylene" refers to a straight chain bridge of 1 to 5 carbon atoms connected by single bonds (e.g., $-(CH_2)_x-$ wherein x is 1 to 5), which may be substituted with 1 to 3 lower alkyl groups.

The term "alkenylene" refers to a straight chain bridge of 2 to 5 carbon atoms having one or two double bonds that is connected by single bonds and may be substituted with 1 to 3 lower alkyl groups. Exemplary alkenylene groups are $-CH=CH-CH=CH-$, $-CH_2-CH=CH-$, $-CH_2-CH=CH-CH_2-$, $-C(CH_3)_2CH=CH-$ and $-CH(C_2H_5)-CH=CH-$.

The term "alkynylene" refers to a straight chain bridge of 2 to 5 carbon atoms that has a triple bond therein, is connected by single bonds, and may be substituted with 1 to 3 lower alkyl groups. Exemplary alkynylene groups are $-C\equiv C-$, $-CH_2-C\equiv C-$, $-CH(CH_3)-C\equiv C-$ and $-C\equiv C-CH(C_2H_5)CH_2-$.

The term "alkanoyl" refers to groups of the formula $-C(O)$alkyl.

The terms "cycloalkyl" and "cycloalkenyl" refer to cyclic hydrocarbon groups of 3 to 8 carbon atoms.

The term "hydroxyalkyl" refers to an alkyl group including one or more hydroxy radicals such as $-CH_2CH_2OH$, $-CH_2CH_2OHCH_2OH$, $-CH(CH_2OH)_2$ and the like.

The terms "halogen" and "halo" refer to fluorine, chlorine, bromine and iodine.

Throughout the specification, groups and substituents thereof are chosen to provide stable moieties and compounds.

The compounds of formula I form salts which are also within the scope of this invention. Pharmaceutically acceptable (i.e., non-toxic, physiologically acceptable) salts are preferred, although other salts are also useful, e.g., in isolating or purifying the compounds of this invention.

The compounds of formula I may form salts with alkali metals such as sodium, potassium and lithium, with alkaline earth metals such as calcium and magnesium, with organic bases such as dicyclohexylamine, t-butyl amine, benzathine, N-methyl-D-glucamide and hydrabamine, and with amino acids such as arginine, lysine and the like. Such salts may be obtained by reacting compound I with the desired ion in a medium in which the salt precipitates or in an aqueous medium followed by lyophilization.

When the $R^1$ to $R^4$ or $R^{11}$ to $R^{14}$ substituents comprise a basic moiety, such as amino or substituted amino, compound I may form salts with a variety of organic and inorganic acids. Such salts include those formed with hydrochloric acid, hydrogen bromide, methanesulfonic acid, sulfuric acid, acetic acid, maleic acid, benzenesulfonate, toluenesulfonate and various other sulfonates, nitrates, phosphates, borates, acetates, tartrates, maleates, citrates, succinates, benzoates, ascorbates, salicylates and the like. Such salts may be formed by reacting compound I in an equivalent amount of the acid in a medium in which the salt precipitates or in an aqueous medium followed by lyophilization.

In addition, when the $R^1$ to $R^4$ or $R^{11}$ to $R^{14}$ substituents comprise a basic moiety such as amino, zwitterions ("inner salts") may be formed.

Certain of the $R^1$ to $R^4$ and $R^{11}$ to $R^{14}$ substituents of compound I may contain asymmetric carbon atoms. Such compounds of formula I may exist, therefore, in enantiomeric and diastereomeric forms and in racemic mixtures thereof. All are within the scope of this invention. Additionally, compound I may exist as enantiomers even in the absence of asymmetric carbons. All such enantiomers are within the scope of this invention.

The compounds of formula I are antagonists of ET-1, ET-2 and/or ET-3 and are useful in treatment of conditions associated with increased ET levels (e.g., dialysis, trauma and surgery) and of all endothelin-dependent disorders. They are thus useful as antihypertensive agents. By the administration of a composition having one (or a combination) of the compounds of this invention, the blood pressure of a hypertensive mammalian (e.g., human) host is reduced. They are also useful in pregnancy-induced hypertension and coma (preeclampsia and eclampsia), acute portal hypertension and hypertension secondary to treatment with erythropoietin.

The compounds of the present invention are also useful in the treatment of disorders related to renal, glomerular and mesangial cell function, including acute and chronic renal failure, glomerular injury, renal damage secondary to old age or related to dialysis, nephrosclerosis (especially hypertensive nephrosclerosis), nephrotoxicity (including nephrotoxicity related to imaging and contrast agents and to cyclosporine), renal ischemia, primary vesicoureteral reflux, glomerulosclerosis and the like. The compounds of this invention may also be useful in the treatment of disorders related to paracrine and endocrine function.

The compounds of the present invention are also useful in the treatment of endotoxemia or endotoxin shock as well as hemorrhagic shock.

The compounds of the present invention are also useful in hypoxic and ischemic disease and as anti-ischemic agents for the treatment of, for example, cardiac, renal and cerebral ischemia and reperfusion (such as that occurring following cardiopulmonary bypass surgery), coronary and cerebral vasospasm, and the like.

In addition, the compounds of this invention may also be useful as anti-arrhythmic agents; anti-anginal agents; anti-fibrillatory agents; anti-asthmatic agents; anti-atherosclerotic and anti-arteriosclerotic agents; additives to cardioplegic solutions for cardiopulmonary bypasses; adjuncts to thrombolytic therapy; and anti-diarrheal agents. The compounds of this invention may be useful in therapy for myocardial infarction; therapy for peripheral vascular disease (e.g., Raynaud's disease and Takayashu's disease); treatment of cardiac hypertrophy (e.g., hypertrophic cardiomyopathy); treatment of primary pulmonary hypertension (e.g., plexogenic, embolic) in adults and in the newborn and pulmonary hypertension secondary to heart failure, radiation and chemotherapeutic injury, or other trauma; treatment of central nervous system vascular disorders, such as stroke, migraine and subarachnoid hemorrhage; treatment of central nervous system behavioral disorders; treatment of gastrointestinal diseases such as ulcerative colitis, Crohn's disease, gastric mucosal damage, ulcer and ischemic bowel disease; treatment of gall bladder or bile duct-based diseases such as cholangitis; treatment of pancreatitis; regulation of cell growth; treatment of benign prostatic hypertrophy; restenosis following angioplasty or following any procedures including transplantation; therapy for congestive heart failure including inhibition of fibrosis; inhibition of left ventricular dilatation, remodeling and dysfunction; and treatment of hepatotoxicity and sudden death. The compounds of this invention may be useful in the treatment of sickle cell disease including the initiation and/or evolution of the pain crises of this disease; treatment of the deleterious consequences of ET-producing tumors such as hypertension resulting from hemangiopericytoma; treatment of early and advanced liver disease and injury including attendant complications (e.g., hepatotoxicity, fibrosis and cirrhosis); treatment of spastic diseases of the urinary tract and/or bladder; treatment of hepatorenal syndrome; treatment of immunological diseases involving vasculitis such as lupus, systemic sclerosis, mixed cryoglobulinemia; and treatment of fibrosis associated with renal dysfunction and hepatotoxicity. The compounds of this invention may be useful in therapy for metabolic and neurological disorders; cancer; insulin-dependent and non insulin-dependent diabetes mellitus; neuropathy; retinopathy; maternal respiratory distress syndrome; dysmenorrhea; epilepsy; hemorrhagic and ischemic stroke; bone remodeling; psoriasis; and chronic inflammatory diseases such as rheumatoid arthritis, osteoarthritis, sarcoidosis and eczematous dermatitis (all types of dermatitis).

The compounds of this invention can also be formulated in combination with endothelin converting enzyme (ECE) inhibitors, such as phosphoramidon; thromboxane receptor antagonists; potassium channel openers; thrombin inhibitors (e.g., hirudin and the like); growth factor inhibitors such as modulators of PDGF activity; platelet activating factor (PAF) antagonists; angiotensin II (AII) receptor antagonists; renin inhibitors; angiotensin converting enzyme (ACE) inhibitors such as captopril, zofenopril, fosinopril, ceranapril, alacepril, enalapril, delapril, pentopril, quinapril, ramipril, lisinopril and salts of such compounds; neutral endopeptidase (NEP) inhibitors; dual NEP-ACE inhibitors; HMG CoA reductase inhibitors such as pravastatin and mevacor; squalene synthetase inhibitors; bile acid sequestrants such as questran; calcium channel blockers; potassium channel activators; beta-adrenergic agents; antiarrhythmic agents; diuretics, such as chlorothiazide, hydrochlorothiazide, flumethiazide, hydroflumethiazide, bendroflumethiazide, methylchlorothiazide, trichloromethiazide, polythiazide or benzothiazide as well as ethacrynic acid, tricrynafen, chlorthalidone, furosemide, musolimine, bumetanide, triamterene, amiloride and spironolactone and salts of such compounds; and thrombolytic agents such as tissue plasminogen activator (tPA), recombinant tPA, streptokinase, urokinase, prourokinase and anisoylated plasminogen streptokinase activator complex (APSAC). If formulated as a fixed dose, such combination products employ the compounds of this invention within the dosage range described below and the other pharmaceutically active agent within its approved dosage range. The compounds of this invention may also be formulated with, or useful in conjunction with, antifungal and immunosuppressive agents such as amphotericin B, cyclosporins and the like to counteract the glomerular contraction and nephrotoxicity secondary to such compounds. The compounds of this invention may also be used in conjunction with hemodialysis.

The compounds of the invention can be administered orally or parenterally to various mammalian species known to be subject to such maladies, e.g., humans, in an effective amount within the dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) in single or 2 to 4 divided daily doses.

The active substance can be utilized in a composition such as tablet, capsule, solution or suspension containing about 5 to about 500 mg per unit dosage of a compound or mixture of compounds of formula I or in topical form for wound healing (0.01 to 5% by weight compound of formula I, 1 to 5 treatments per day). They may be compounded in a conventional manner with a physiologically acceptable vehicle or carrier, excipient, binder, preservative, stabilizer, flavor, etc., or with a topical carrier such as Plastibase (mineral oil gelled with polyethylene) as called for by accepted pharmaceutical practice.

The compounds of the invention may also be administered topically to treat peripheral vascular diseases and as such may be formulated as a cream or ointment.

The compounds of formula I can also be formulated in compositions such as sterile solutions or suspensions for parenteral administration. About 0.1 to 500 milligrams of a compound of formula I is compounded with a physiologically acceptable vehicle, carrier, excipient, binder, preservative, stabilizer, etc., in a unit dosage form as called for by accepted pharmaceutical practice. The amount of active substance in these compositions or preparations is such that a suitable dosage in the range indicated is obtained.

The compounds of the present invention may be prepared as follows.

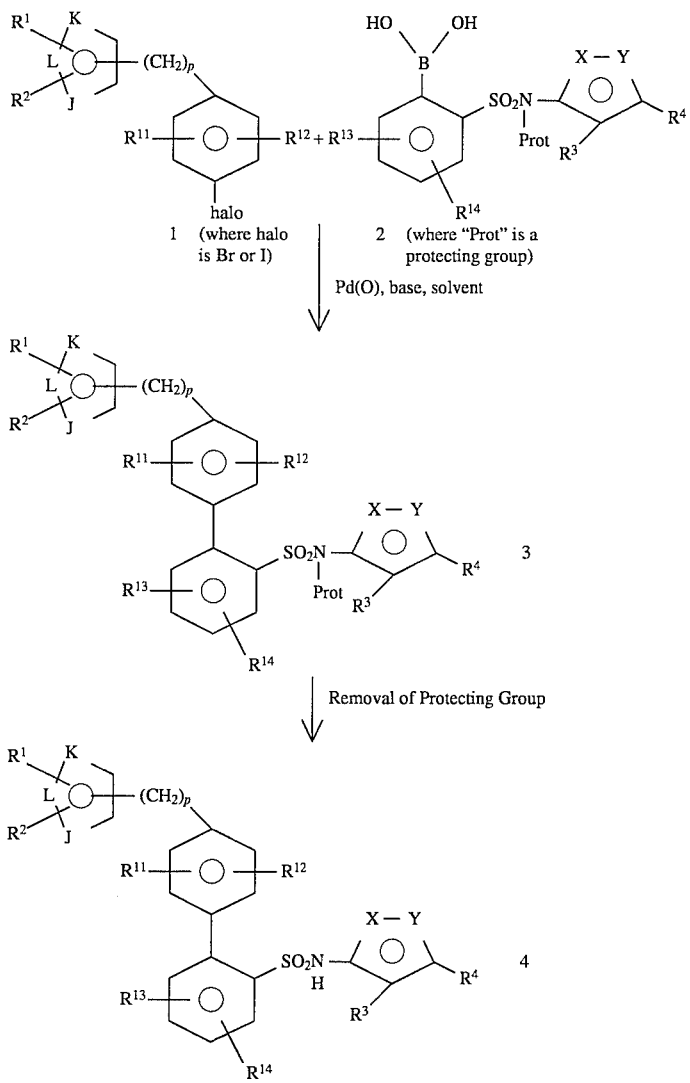

As depicted by the above Scheme I, the title compounds 4 may be prepared by a Pd(O) catalyzed coupling of an appropriately protected phenylsulfonamide-2-boronic acid intermediate 2 with a 4-heterocyclic aryl halide 1 in the presence of a suitable base, such as aqueous potassium carbonate, and solvent, such as a mixture of toluene and ethanol.

A boronic acid intermediate 2 may be prepared from a 2-bromophenylsulfonamide 5 (preparation of which is described in EP Publication number 0,569,193 (1993)) by lithiation with a suitable alkyl lithium (such as n-butyl lithium), subsequent treatment with a trialkylborate (e.g., triisopropyl borate) and finally adding an aqueous acid such as aqueous hydrochloric acid (SCHEME II):

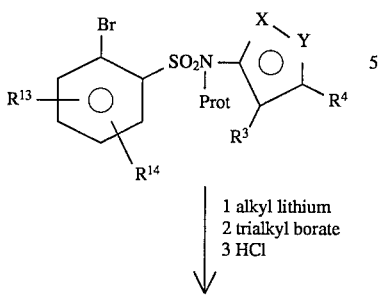

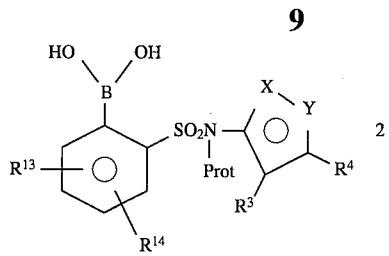

"Prot" is an appropriate protecting group for the sulfonamide function, also described in EP Publication number 0,569,193 (1993).

The title compounds may also be synthesized by an alternate route shown below (SCHEME III):

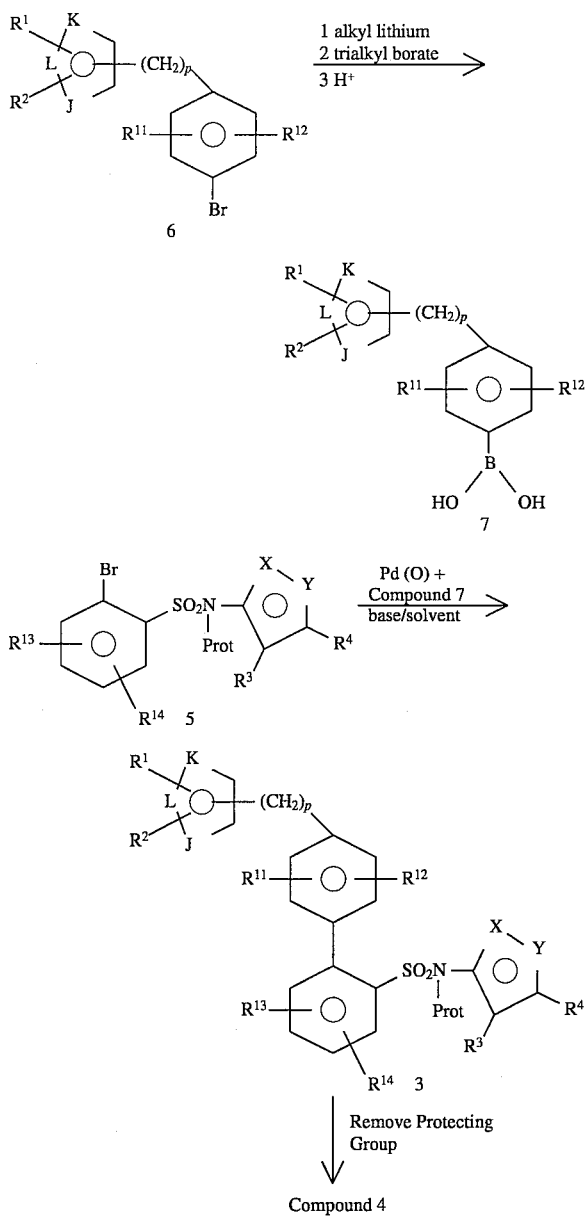

As depicted above, a 4'-Heterocyclic aryl halide 6 (see also compound 1) can be converted to a boronic acid intermediate 7 via the sequence shown. This compound 7, upon Pd(O) catalyzed coupling with a compound 5 can provide a biaryl analog 3, which upon deprotection can lead to the title compound 4. In certain instances, the heteroatoms J and K or L may require protection to prepare the boronic acid 7, and/or to facilitate the coupling reaction to make compound 3. (For example, when J and K or L are N, one of the groups may be protected by a suitable protecting group such as t-butoxycarbonyl, etc). Also, in certain instances, the boronic acid may be replaced with a tin species and/or the halo group may be replaced by a —$OSO_2CF_3$ moiety to perform the Pd-catalyzed coupling reaction. For general strategies in biaryl synthesis, see: Bringmann et al., *Angew. Chem. Inst.*, Ed. Engl. 29 (1990) 977–991.

SYNTHESES OF COMPOUNDS 1 AND 6

Compounds 1 and 6 can be prepared by the following Schemes. 2-Aryloxazoles are prepared as depicted by SCHEME IV, Methods A–H; 4-Aryloxazoles are prepared as depicted by SCHEME V, Methods A–B; 5-Aryloxazoles are prepared as depicted by SCHEME VI, Methods A–B; Thiazoles are prepared as depicted by SCHEME VII, Methods A–B; Imidazoles are prepared as depicted by SCHEME VIII; 2-Phenylalkyloxazoles are prepared as depicted by SCHEME IX, Methods A–B; Pyrazoles are prepared as depicted by SCHEME X; 3-Arylisoxazoles are prepared as depicted by SCHEME XI; 5-Arylisoxazoles are prepared as depicted by SCHEME XII; and N-Arylimidazoles are prepared as depicted by SCHEME XIII.

A. 2-Aryloxazoles

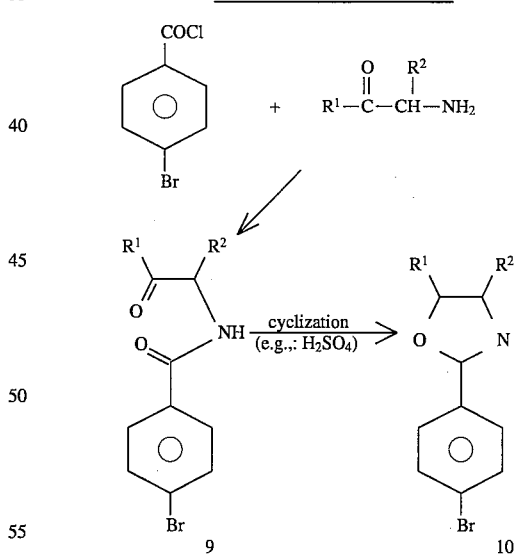

An acyl amino compound 9 is prepared as depicted above and may be cyclized to an oxazole 10 using a variety of dehydrating agents. For a review of this and other methods of oxazole synthesis, see: Lakhan et al., *Adv, Het. Chem.*, 17 (1974), 99.

SCHEME IV. Method B

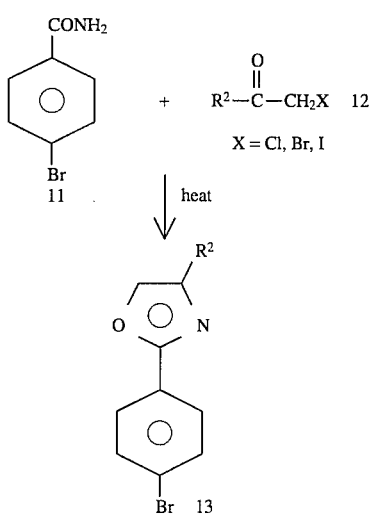

As shown, heating together a mixture of a benzamide 11 and an α-halo carbonyl compound 12 provides the corresponding oxazole 13. This method has been used extensively to provide 2,4-disubstituted oxazoles. For a review, see: Lakhan et al., *Adv. Het. Chem.*, 17, (1979) 99–211.

SCHEME IV. Method C

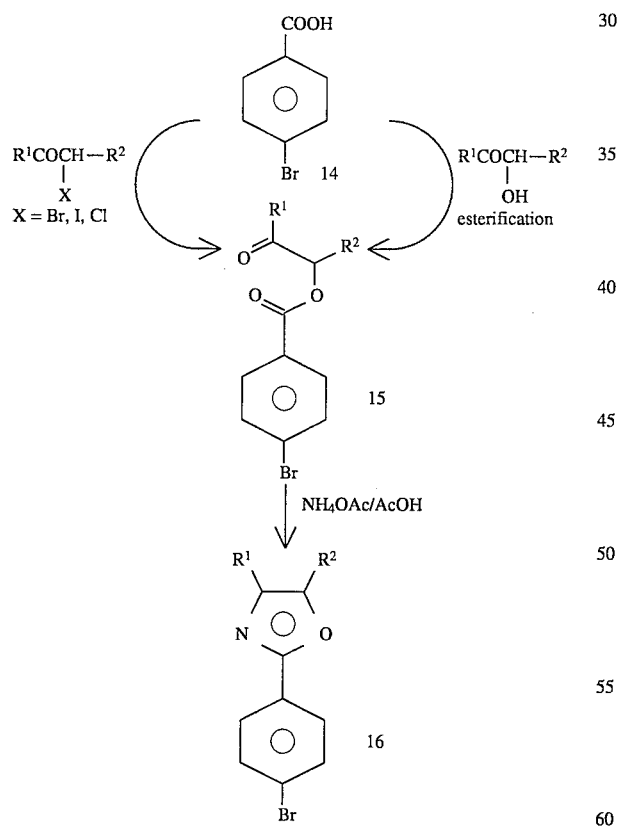

An ester 15 can be prepared either by allowing an α-haloketone to react with a benzoic acid 14 in the presence of a base such as triethylamine, or by esterification with an appropriate α-hydroxyketone. Compound 15, upon treatment with ammonium acetate in acetic acid, provides an oxazole 16.

SCHEME IV. Method D

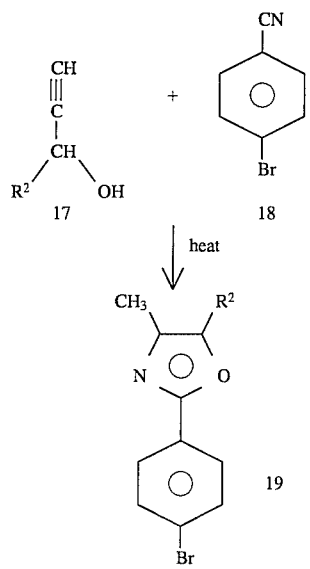

Certain acetylenic carbinols such as compound 17 can react directly with an arylnitrile 18 to provide a 5-methyl oxazole, 19. (See, for example, Y. Yura, Japanese Patent 29849 (1964).)

SCHEME IV. Method E

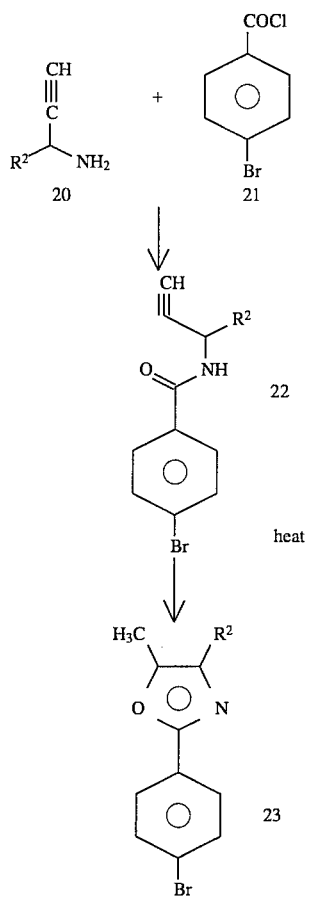

An acetylenic amide 22, upon heating, cyclizes to an oxazole derivative 23.

SCHEME IV. Method F

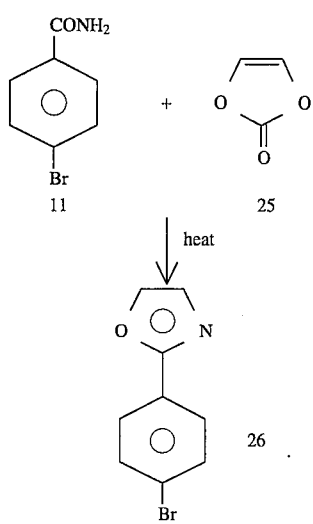

A 4,5-unsubstituted oxazole 26 may be prepared by condensing a 4-bromobenzamide 11 with a vinylene carbonate 25 at high temperature in the presence of an agent such as polyphosphoric acid. (See, for example, Ferrini, et al., *Angew. Chem. Internat. Ed.*, Vol. 2, 1963, 99.)

SCHEME IV. Method G

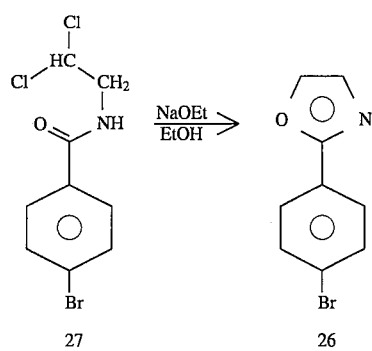

Cyclization of the N-(2,2-dichloroethyl)amide derivative 27, prepared by methods known in the art, in the presence of a suitable base such as sodium ethoxide, may also provide the oxazole derivative 26. (See, for example, U.S. Pat. No. 3,953,465.)

SCHEME IV. Method H

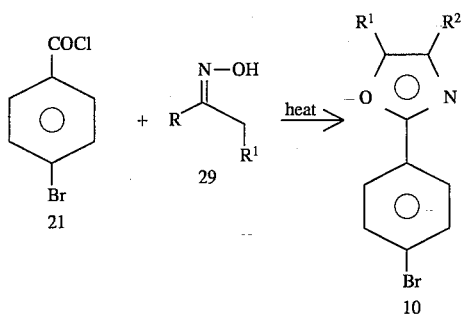

Heating together a mixture of aroylchloride 21 with an oxime 29 where $R^1$ and $R^2$ are alkyl, prepared by methods known in the art, may provide the oxazole derivative 10. (See, for example, Bhatt, M. V. and Reddy, A. S., *Tet. Lett.*, 21, 2359 (1980).)

SCHEME IV. Method I

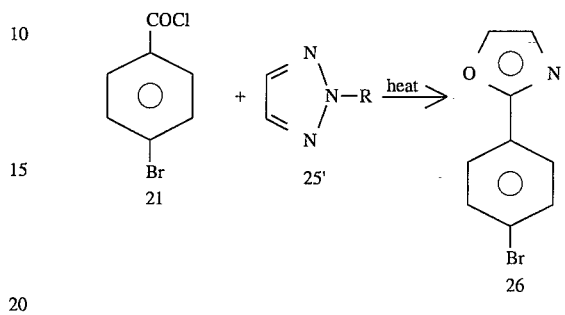

Heating together a mixture of aroylchloride 21 with a triazole 25' where R is trimethylsilyl, prepared by methods known in the art, in a suitable solvent such as toluene may provide the oxazole derivative 26. (See, for example, Williams, E. L., *Tet. Lett.*, 33, 1033–1036 (1992).)

It is also possible to prepare the oxazole derivative 26 by treatment of aroylchloride 21 with triazole (where R is hydrogen) in the presence of suitable base such as potassium carbonate followed by heating the mixture to an optimal temperature.

B. 4-Aryloxazoles

SCHEME V. Method A

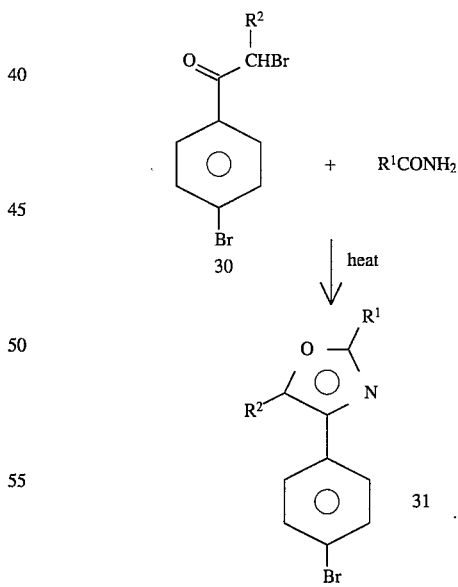

Treatment of an α-Bromoacetophenone derivative 30 with an amide at high temperatures (typically 130°–150° C.) provides a 4-aryl oxazole 31.

SCHEME V. Method B

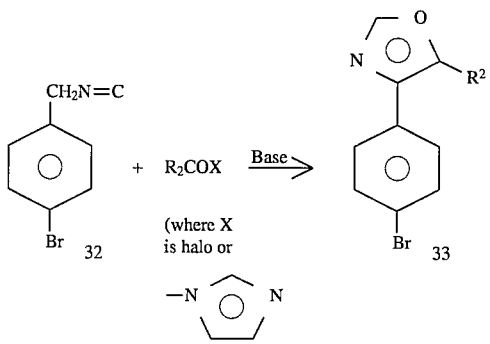

Certain α-metallated isonitriles 32, prepared by methods known in the art, react with acyl halides, imidazoles or other activated acyl groups, to provide 2-unsubstituted oxazoles 33 where $R^2$ is alkyl or aryl.

C. 5-Aryoxazoles

SCHEME VI. Method A

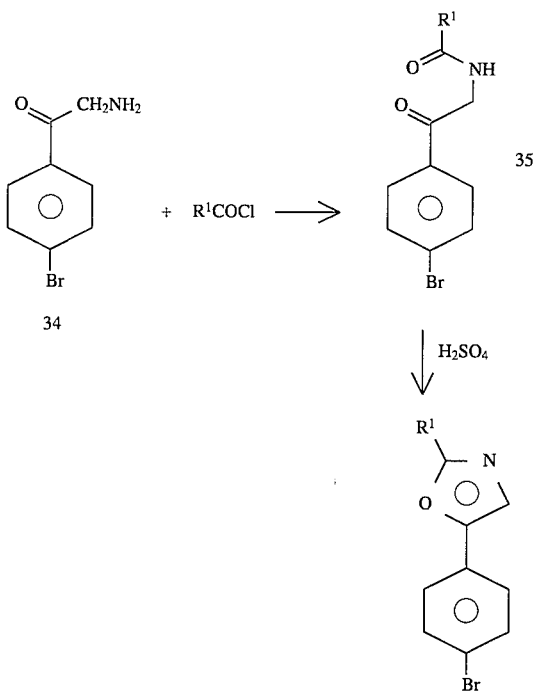

Acylation of an α-aminoacetophenone 34, with an acyl chloride, provides compound 35. Compound 35, upon cyclization using a suitable dehydrating agent such as sulfuric acid, provides an oxazole 36. (This method is similar to the one described in SCHEME IV, Method A).

SCHEME VI. Method B

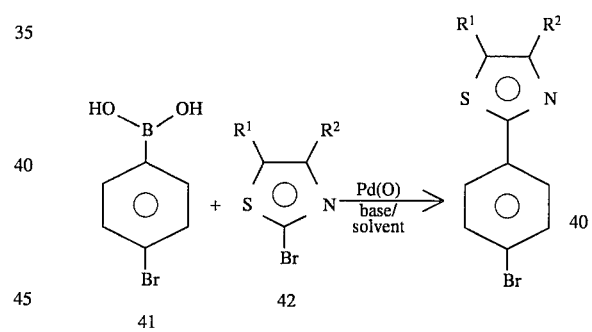

A 4-Halobenzaldehyde 37 is treated with tosylmethylisocyanide 38 in the presence of a base, such as potassium carbonate, in a suitable solvent, such as methanol, to provide a 5-aryloxazole derivative 39. (See, for example, A. M. Van Leusen, et al., *Tet. Lett.*, 2369 (1972).)

D. Thiazoles

SCHEME VII. Method A

A 4-Bromophenyl boronic acid 41 can be coupled with an appropriately substituted 2-bromothiazole 42 in the presence of a Pd(O) catalyst and a suitable base (e.g., aqueous potassium carbonate) and solvent to provide a thiazole 40.

SCHEME VII.
Method B

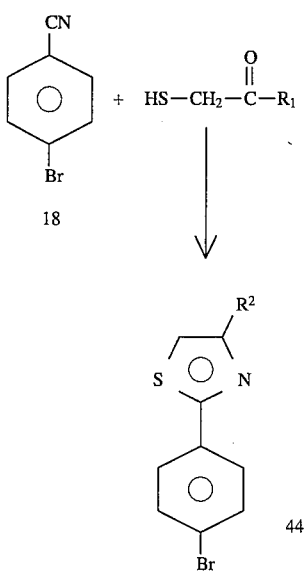

Condensation of p-bromobenzonitrile 18 with an α-thioketone directly provides a thiazole derivative 44.

E. Imidazoles

SCHEME VIII

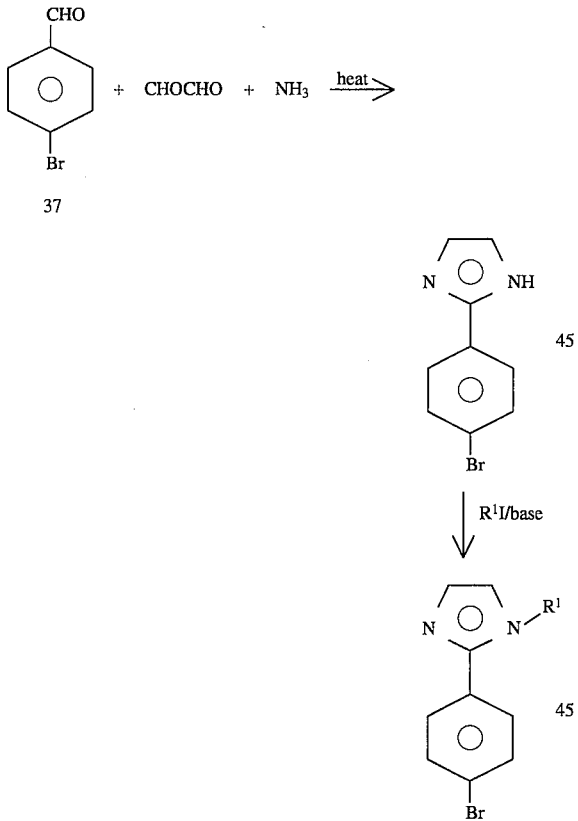

Condensation of a benzaldehyde derivative 37 with glyoxal and ammonia provides a 2-aryl imidazole derivative 45. (See, e.g., U.S. Pat. No. 3,682,949.) This compound can be further substituted by reacting it with an alkyl halide in the presence of a suitable base to provide, e.g., an N-alkyl-derivative 46.

For a review on imidazole synthesis, see: *Adv. Het. Chem.*, 27, (1980), 241–323.

F. 2-Phenylalkyloxazoles

SCHEME IX.
Method A

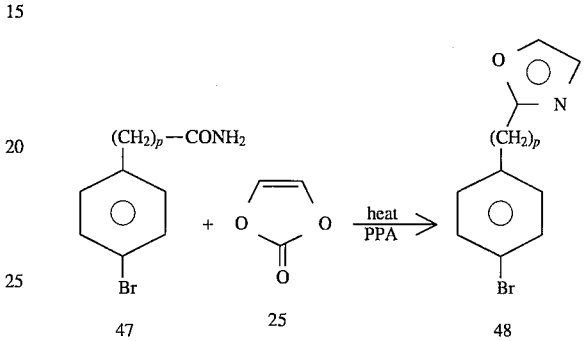

2-Phenylalkyloxazoles 48, where p is 1 or 2, unsubstituted at the 4 and 5 positions, may be prepared by heating together a phenylalkylamide 47 with vinylene carbonate 25 in the presence of an agent such as polyphosphoric acid.

SCHEME IX.
Method B

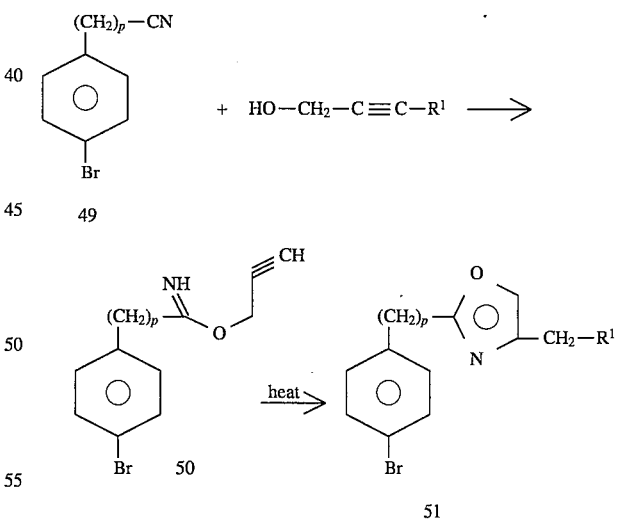

2-Arylalkyl-4-substituted-oxazole 51, where $R^1$ is alkyl and n is 1 or 2, may be prepared starting from a nitrile 49 as shown above. (See, for example, U.S. Pat. No. 4,168,379.)

G. Pyrazoles

SCHEME X

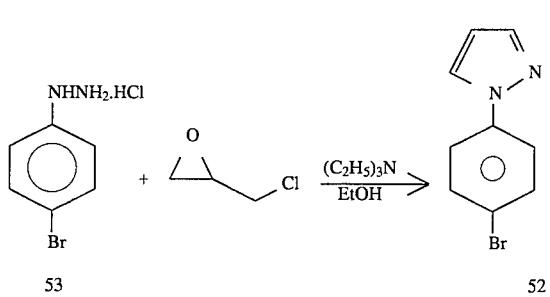

The pyrazole derivative 52 may be prepared by heating together the aryl hydrazine 53 with epichlorohydrin in the presence of a suitable base such as triethyl amine.

H. 3-Arylisoxazoles

SCHEME XI

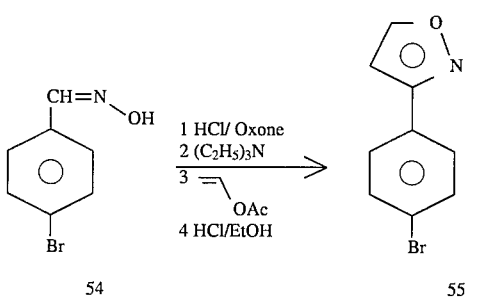

Treatment of the oxime 54, prepared by methods know in the art, with HCl/Oxone, and subsequent treatment with a base such as triethylamine, provides an arylnitrile oxide. The arylnitrile oxide typically is not isolated, but is reacted with vinylacetate, and then the mixture is heated in an acid (e.g., HCl) in a suitable solvent such as ethanol to provide the 3-aryl isoxazole derivative 55.

I. 5-Arylisoxazoles

SCHEME XII

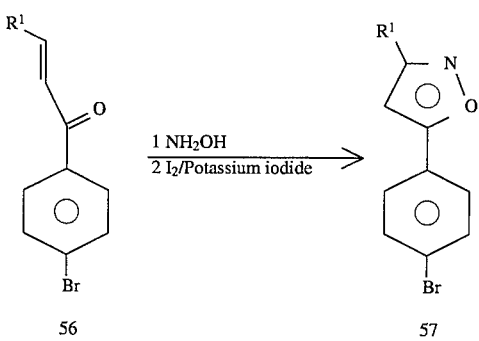

An α,β-unsaturated ketone 56, prepared by methods known in the art, upon treatment with hydroxylamine provides the corresponding oxime derivative. Cyclization of this material in the presence of iodine and potassium iodide provides the 5-arylisoxazole derivative 57. $R^1$ in this scheme is alkyl or aryl. (See for example, *J. Het. Chem.*, 30, 467 (1993).)

J. N-Arylimidazoles

SCHEME XIII

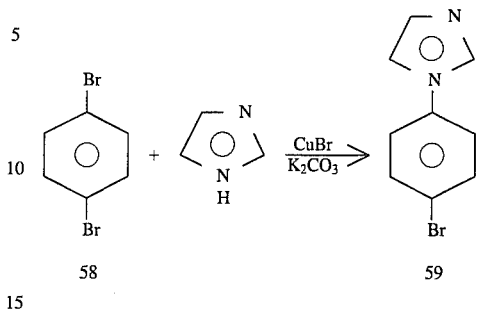

The N-arylimidazole analog 59 may be prepared by a standard Ullmann coupling, known in the art, of the 1,4-dibromobenzene 58 with imidazole in the presence of a copper salt such as CuBr.

The invention will now be further described by the following working examples, which are preferred embodiments of the invention. These examples are meant to be illustrative rather than limiting.

EXAMPLE 1

N-(3,4-Dimethyl-5-isoxazolyl)-4'-(2-oxazolyl)[1,1'-biphenyl]-2-sulfonamide

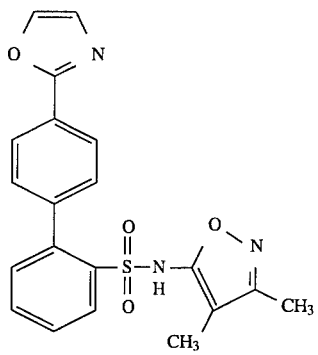

A. 2-(4-Bromophenyl)oxazole

A mixture of 4-bromobenzenecarboxamide (4 g, 20 mmol), vinylene carbonate (1.72 g, 20 mmol) and 10 g polyphosphoric acid was heated at 170° C. for 3 hours. After cooling, the mixture was partitioned between 200 mL water and 200 mL ethyl acetate. The aqueous layer was extracted with 2×150 mL ethyl acetate. The combined organic liquid was washed with 100 mL water and 50 mL brine, dried and concentrated. The residue was chromatographed on silica gel using 10:1 hexane/ethyl acetate to afford compound A (2.49 g, 56%) as a white solid.

B. 2-Borono-N-(3,4-dimethyl-5-isoxazolyl)-N'-(methoxyethoxymethyl)benzenesulfonamide To a solution of 2-Bromo-N-(3,4-dimethyl-5-isoxazolyl)-N'-(methoxyethoxymethyl)benzenesulfonamide (5.67 g, 13.52 mmol, prepared as described in EP 0,569,193 (1993)) in 70 mL of tetrahydrofuran at −78° C., n-butyl lithium (2M solution in cyclohexane, 8.11 mL, 16.23 mmol) was added over 10 minutes. The resulting solution was stirred at −78° C. for 15 minutes and triisopropylborate (1.52 g, 8.06 mmol) was added. The mixture was then warmed to room temperature and stirred for 2 hours. The mixture was cooled to 0° C., 10% aqueous hydrochloric acid (120 mL) was added, and the solution was stirred for 10 minutes. The mixture was concentrated to 120 mL and extracted with 4×60 mL ethyl acetate. The combined organic extracts were washed once with 100 mL brine, dried (MgSO$_4$) and concentrated to give compound B (4.25 g, 82%) as a light yellow gum.

C. N-(3,4-Dimethyl-5-isoxazolyl)-N-[(2-methoxyethoxy)methyl]-4'-(2-oxazolyl)[1,1'-biphenyl]-2-sulfonamide To a solution of compound B (315 mg, 0.82 mmol), compound A (456 mg, 2.05 mmol) in 7.5 ml of toluene and 6 mL of 95% ethanol under argon, tetrakis (triphenylphosphine)palladium(O) (95 mg, 0.082 mmol) was added, followed by 4.5 mL of 2M aqueous sodium carbonate. The reaction mixture was heated at 75° C. for 4 hours, cooled and diluted with 50 mL of ethyl acetate. The organic liquid was separated and washed with 10 mL water and 10 mL brine, dried and concentrated. The residue was chromatographed on silica gel using 2:1 hexane/ethyl acetate to afford compound C (279 mg, 70%) as a colorless gum.

D. N-(3,4-Dimethyl-5-isoxazolyl)-4'-(2-oxazolyl)[1,1'-biphenyl]-2-sulfonamide

To a solution of compound C (276 mg, 0.57 mmol) in 10 mL of 95% ethanol, 10 mL of 6N aqueous hydrochloric acid was added and refluxed for 1 hour and 10 minutes. The reaction mixture was concentrated and the pH of the solution was adjusted to 8 using sodium bicarbonate solution. It was then acidified to pH 5 with glacial acetic acid. The mixture was extracted with 3×40 mL ethyl acetate. The organic liquid was washed with 10 mL water and 10 mL brine, dried and concentrated. The residue was chromatographed on silica gel using 100:1 dichloromethane/methanol to afford the title compound (117 mg, 52%) as a white solid.

M.p. 90°–98° C.(amorphous).

Analysis calculated for $C_{20}H_{17}N_3O_4S$: Calculated: C, 60.75; H, 4.33; N, 10.63; S, 8.11; Found: C, 60.80; H, 4.15; N, 10.38; S, 8.12.

EXAMPLE 2

N-(3,4-Dimethyl-5-isoxazolyl)-4'-(2-thiazolyl)[1,1'-biphenyl]-2-sulfonamide

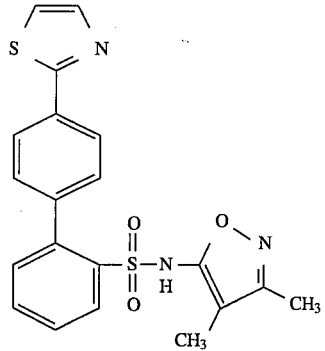

A. 2-(4-Bromophenyl)thiazole

To a solution of 4-Bromophenylboronic acid (3.01 g, 15 mmol), 2-bromothiazole (9.84 g, 60 mmol) in 120 mL of toluene and 96 mL of 95% ethanol under argon, tetrakis(triphenylphosphine)palladium(O) (1.04 g, 0.9 mmol) was added, followed by 72 mL of 2M aqueous sodium carbonate. The reaction mixture was heated at 75° C. for 1 hour and 15 minutes, cooled and diluted with 300 mL of ethyl acetate. The organic liquid was separated and washed with 100 mL water and 100 mL brine, dried and concentrated. The residue was chromatographed on silica gel using 30:1 Hexane/ethyl acetate to afford compound A (2.0 g, 56%) as a white solid.

B. N-(3,4-Dimethyl-5-isoxazolyl)-N-[(2-methoxyethoxy)methyl]-4'-(2-thiazoyl)[1,1'-biphenyl]-2-sulfonamide To a solution of compound B from Example 1 (320 mg, 0.83 mmol) and compound A (400 mg, 1.67 mmol) in 7.5 mL of toluene and 6 mL of 95% ethanol under argon, tetrakis(triphenyl-phosphine)palladium(O) (96 mg, 0.083 mmol) was added, followed by 4.5 mL of 2M aqueous sodium carbonate. The reaction mixture was heated at 75° C. for 3 hours cooled and diluted with 50 ml of ethyl acetate. The organic liquid was separated and washed with 10 mL water and 10 mL brine, dried and concentrated. The residue was chromatographed on silica gel using 2.5:1 hexane/ethyl acetate to afford compound B (291 mg, 70%) as a colorless gum.

C. N-(3,4-Dimethyl-5-isoxazolyl)-4'-(2-thiazolyl)[1,1'-biphenyl]-2-sulfonamide

To a solution of compound B (290 mg, 0.58 mmol) in 10 mL of 95% ethanol, 10 mL of 6N aqueous hydrochloric acid was added and refluxed for 1 hour. The reaction mixture was concentrated and the pH of the solution was adjusted to 8 using sodium bicarbonate solution. It was then acidified to pH 5 with glacial acetic acid. The mixture was extracted with 3×40 mL ethyl acetate. The organic liquid was washed with 10 mL water and 10 mL brine, dried and concentrated. The residue was chromatographed on silica gel using 100:1 dichloromethane/methanol to afford the title compound (180 mg, 75%) as an off-white solid.

M.p. 87°–97° C.(amorphous).

Analysis calculated for $C_{20}H_{17}N_3O_3S_2 \cdot 0.34H_2O$: Calculated: C, 57.52; H, 4.27; N, 10.06; S, 15.35; Found: C, 57.68; H, 4.08; N, 9.90; S, 15.06.

EXAMPLE 3

N-(3,4-Dimethyl-5-isoxazolyl)-4'-(4,5-dimethyl-2-oxazolyl)[1,1'-biphenyl]-2-sulfonamide

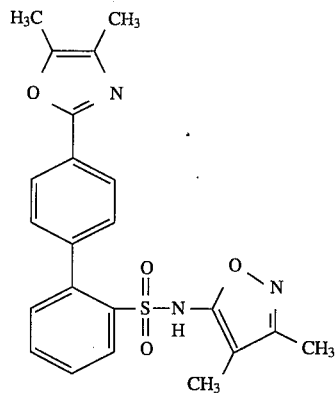

A. 4-Bromobenzoic acid, 2-oxo-1-methylpropyl ester

To 3-hydroxy-2-butanone (1.32 g, 15 mmol) and 4-bromobenzoyl chloride (3.29 g, 15 mmol) in 15 mL dichloromethane at 0° C., 5 mL pyridine was added dropwise. The reaction was stirred at room temperature for 5 hours, 150 mL ethyl acetate was added and filtered. The filtrate was washed with 2×50 mL 10% hydrochloric acid, 30 mL water and 30 mL brine, dried and concentrated. The residue was chromatographed on silica gel using 10:1 hexane/ethyl acetate to afford compound A (3.4 g, 84%) as a white solid.

B. 2-(4-Bromophenyl)-4,5-dimethyloxazole

A mixture of compound A (3.4 g, 12.54 mmol), ammonium acetate (9.67 g, 125.4 mmol) and 10 mL acetic acid was heated at 100° C. for 4 hours. After cooling, the mixture was partitioned between 150 mL water and 200 mL ethyl acetate. The organic liquid was washed with 50 mL water and 50 mL brine, dried and concentrated. The residue was chromatographed on silica gel using 25:1 hexane/ethyl acetate to afford compound B (1.52 g, 48%) as a white solid.

C. N-(3,4-Dimethyl-5-isoxazolyl)-4'-(4,5-dimethyl-2-oxazolyl)-N-[(2-methoxyethoxy)methyl][1,1'-biphenyl]-2-sulfonamide To a solution of compound B from Example 1 (320 mg, 0.83 mmol) and compound B above (420 mg, 1.67 mmol) in 7.5 mL of toluene and 6 ml of 95% ethanol under argon, tetrakis(triphenylphosphine)palladium(O) (96 mg, 0.083 mmol) was added, followed by 4.5 mL of 2M aqueous sodium carbonate. The reaction mixture was heated at 75° C. for 4 hours, cooled and diluted with 50 mL of ethyl acetate. The organic liquid was separated and washed with 10 mL water and 10 mL brine, dried and concentrated. The residue was chromatographed on silica gel using 2:1 hexane/ethanol to afford compound C (300 mg, 70%) as a colorless gum.

D. N-(3,4-Dimethyl-5-isoxazolyl)-4'-(4,5-dimethyl-2-oxazolyl)[1,1'-biphenyl]-2-sulfonamide To a solution of compound C (300 mg, 0.59 mmol) in 10 mL of 95% ethanol, 10 mL of 6N aqueous hydrochloric acid was added and refluxed for 1 hour. The reaction mixture was concentrated, and the pH of the solution was adjusted to 8 using sodium bicarbonate solution. It was then acidified to pH 5 with glacial acetic acid. The mixture was extracted with 3×40 ml ethyl acetate. The organic liquid was washed with 10 mL water and 10 mL brine, dried and concentrated. The residue was chromatographed on silica gel using 1:1 hexane/ethyl acetate to afford the title compound (178 mg, 72%) as a white solid.

M.p. 96°–102° C.(amorphous).

Analysis calculated for $C_{22}H_{21}N_3O_4S \cdot 0.24H_2O$: Calculated: C, 61.76; H, 5.06; N, 9.82; S, 7.49; Found: C, 61.67; H, 4.76; N, 9.91; S, 7.59.

EXAMPLE 4

N-(3,4-Dimethyl-5-isoxazolyl)-4'-(5-oxazolyl)[1,1'-biphenyl]-2-Sulfonamide

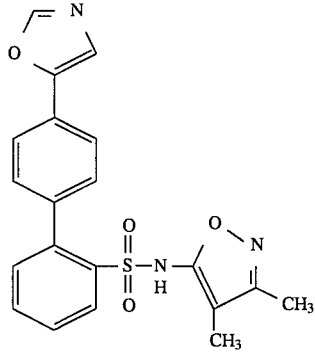

A. 5-(4-Bromophenyl)oxazole

A mixture of 4.74 g (25.6 mmol) of p-bromobenzaldehyde, 5.0 g (25.6 mmol) of tosylmethyl isocyanide and 4.25 g (30.7 mmol) of anhydrous potassium carbonate in 150 mL of methanol was refluxed for 3 hours. The solvent was then evaporated, and 150 mL of water was added to the residual solid. The tan-white solid was filtered and washed several times with water and then dried to yield compound A (3.65 g, 64%).

B. N-(3,4-Dimethyl-5-isoxazolyl)-N-[(2-methoxyethoxy)methyl]-4'-(5-oxazolyl)[1,1'-biphenyl]-2-sulfonamide To a solution of 0.8 g (2.08 mmol) compound B from Example 1 and 0.12 g (0.1 mmol) of tetrakis(triphenylphosphine)-palladium(O) in 25 mL of toluene under argon, 15 mL of 2M aqueous sodium carbonate was added followed by 0.70 g (3.12 mmol) of compound A in 15 mL of 95% ethanol. The mixture was refluxed for 3 hours, diluted with 100 mL of water and extracted with 3×75 mL of ethyl acetate. The combined organic extracts were washed once with 100 mL of brine, dried and evaporated. The residue was chromatographed on 50 g of silica gel using Hexanes/ethyl acetate 2:1 to afford 0.49 g (49%) of compound B as a colorless gum.

C. N-(3,4-Dimethyl-5-isoxazolyl)-4'-(5-oxazolyl)[1,1'-biphenyl]-2-sulfonamide

To a solution of 0.49 g (1.01 mmol) of compound B in 10 mL of 95% ethanol, 10 mL of 6N aqueous hydrochloric acid was added and refluxed for 1 hour. The mixture was then concentrated and diluted with 50 mL of water. The solution was neutralized to pH 7 using saturated aqueous sodium bicarbonate and then acidified to pH 4 using glacial acetic acid. The white solid obtained was filtered and dried (0.37 g). Crystallization from dichloromethane/ethyl acetate/Hexanes afforded 0.23 g (58%) of the title compound as a white solid.

M.p. 189°–191° C.

Analysis Calculated for $C_{20}H_{17}N_3O_4S \cdot 0.28 \, H_2O$: C, 60.00; H, 4.42; N, 10.49; S, 8.01; Found: C, 60.10; H, 4.17; N, 10.39; S, 8.04.

EXAMPLE 5

N-(3,4-Dimethyl-5-isoxazolyl)-4'-(4-oxazolyl)[1,1'-biphenyl]-2-sulfonamide

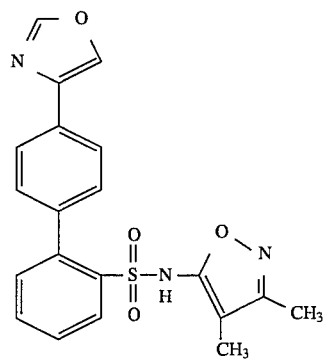

A. 4-(4-Bromophenyl)oxazole

A mixture of 5.0 g (18 mmol) of α, p-dibromoacetophenone and 4.05 g (89.9 mmol) of formamide was stirred in an oil bath at 130° C. for 3 hours. The mixture was then poured into 150 mL of ice/water and the solution was extracted with 3×100 mL of ether. The combined ether extracts were washed once with water, dried and evaporated. The residue was chromatographed on 200 mL of silica gel using Hexanes/ethyl acetate 3:1 to afford 1.3 g (32%) of compound A as a light brown solid.

B. N-(3,4-Dimethyl-5-isoxazolyl)-N-[(2-methoxyethoxy)methyl]-4'-(4-oxazolyl)[1,1'-biphenyl]-2-sulfonamide To a solution of 0.668 g (1.74 mmol) of compound B from Example 1 and 0.104 g (0.09 mmol) of tetrakis(tri-phenylphosphine)palladium(O) in 25 mL of toluene under argon, 15 mL of 2M aqueous sodium carbonate was added followed by 0.52 g (2.32 mmol) of compound A in 15 mL of 95% ethanol. The mixture was refluxed for 3 hours, diluted with 100 mL of water and extracted with 3×75 mL of ethyl acetate. The combined organic extracts were washed once with 100 mL of brine, dried and evaporated. The residue was chromatographed on 50 g of silica gel using Hexanes/ethyl acetate 2:1 to afford 0.43 g (51%) of compound B as a colorless gum.

C. N-(3,4-Dimethyl-5-isoxazolyl)-4'-(4-oxazolyl)[1,1'-biphenyl]-2-sulfonamide

To a solution of 0.75 g (1.55 mmol) of compound B in 8 mL of acetonitrile at 0° C. under argon, trimethylsilyl chloride (2.01 g) and sodium iodide (2.73 g) were added and the mixture was stirred at room temperature for 1 hour. The mixture was then diluted with 10 mL of water and extracted with 100 mL of ethyl acetate. The organic layer was washed with 10 mL of saturated aqueous sodium thiosulfate, dried and evaporated. This material was purified by reverse phase preparative HPLC on 30×500 mm ODS S10 column using 68% solvent A (90% methanol, 10% water, 0.1% trifluoroacetic acid) and 32% solvent B (10% methanol, 90% water, 0.1% trifluoroacetic acid). The appropriate fractions were collected and neutralized with aqueous sodium bicarbonate to pH 7 and concentrated to 10 mL. The solution was acidified to pH 4 using glacial acetic acid and the white solid was filtered and dried to provide 0.33 g (54%) of the title compound.

M.p. 85°–93° C. (amorphous).

Analysis Calculated for $C_{20}H_{17}N_3O_4S \cdot 0.21\ H_2O$: C, 60.18; H, 4.40; N, 10.53; S, 8.03; Found: C, 60.27; H, 4.05; N, 10.44; S, 7.88.

B. N-(3,4-Dimethyl-5-isoxazolyl)-N-[(2-methoxyethoxy)methyl]-4'-(2-methyl-4-oxazolyl)[1,1'-biphenyl]-2-sulfonamide To a solution of compound A (402 mg, 1.7 mmol) and compound B from Example 1 (259 mg, 0.68 mmol) in 6.5 mL of toluene and 5.2 mL of 95% ethanol under argon, tetrakis (triphenylphosphine)palladium(O) (78 mg, 0.068 mmol) was added and followed by 3.9 mL of 2M aqueous sodium carbonate. The reaction mixture was heated at 75° C. for 3.5 hours, cooled and diluted with 40 mL of ethyl acetate. The organic liquid was separated and washed with 10 mL water and 10 mL brine, dried and concentrated. The residue was chromatographed on silica gel using 2:1 hexane/ethyl acetate to afford compound B (183 mg, 54%) as a colorless gum.

C. N-(3,4-Dimethyl-5-isoxazolyl)-4'-(2-methyl-4-oxazolyl)[1,1'-biphenyl]-2-sulfonamide To a solution of compound B (180 mg, 0.36 mmol) in 6 mL of 95% ethanol, 6 mL of 6N aqueous hydrochloric acid was added and the combination was refluxed for 55 minutes. The reaction mixture was concentrated and the pH of the solution was adjusted to 8 using sodium bicarbonate solution. It was then acidified to pH 5 with glacial acetic acid. The mixture was extracted with 3×30 mL ethyl acetate. The organic liquid was washed with 10 mL brine, dried and concentrated. The residue was chromatographed on silica gel using 100:1 dichloromethane/methanol to afford the title compound (56 mg, 38%) as a light yellow solid.

M.p. 90°–100° C.(amorphous).

Analysis calculated for $C_{21}H_{19}N_3O_4S$: Calculated: C, 61.60; H, 4.68; N, 10.26; S, 7.83; Found: C, 61.56; H, 4.33; N, 9.85; S, 7.94.

EXAMPLE 6

N-(3,4-Dimethyl-5-isoxazolyl)-4'-(2-methyl-4-oxazolyl)[1,1'-biphenyl]-2-sulfonamide

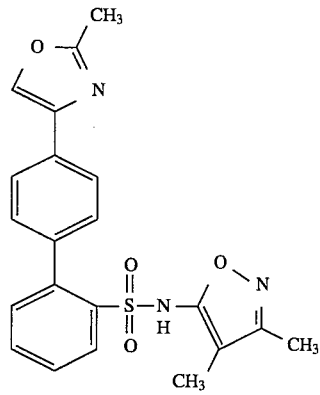

A. 4-(4-Bromophenyl)-2-methyloxazole

A mixture of 2,4-dibromoacetophenone (2.78 g, 10 mmol) and acetamide (1.48 g, 25 mmol) was heated at 130° C. for 3 hours. This mixture was poured onto 30 g ice, and 150 mL ethyl acetate was added. The organic layer was separated and washed with 30 mL 1N sodium hydroxide, 30 mL 1N hydrochloric acid and 30 mL brine, dried and concentrated. The residue was chromatographed on silica gel using 15:1 hexane/ethyl acetate to afford compound A (1.29 g, 54%) as a white solid.

EXAMPLE 7

N-(3,4-Dimethyl-5-isoxazolyl)-4'-(4-methyl-2-oxazolyl)[1,1'-biphenyl]-2-sulfonamide

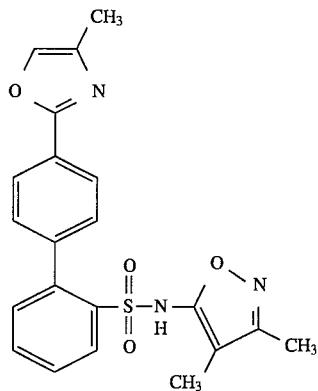

A. 2-(4-Bromophenyl)-4-methyloxazole 4-bromobenzonitrile (9.1 g, 50 mmol) and propargyl alcohol (2.8 g, 50 mmol) were added portionwise into 12.5 mL concentrated sulfuric acid at −15° C. The reaction was stirred at 0° C. for 3 hours, warmed to room temperature slowly and stirred overnight. The mixture was poured into 200 mL ice water, neutralized with sodium bicarbonate and extracted with 3×200 mL ethyl acetate. The combined organic liquid was washed with 50 mL brine, dried and concentrated. The residue was chromatographed on silica gel using 30:1 Hexane/ethyl acetate to afford compound A (1.44 g, 12%) as a white solid.

B. N-(3,4-Dimethyl-5-isoxazolyl)-N-[(2-methoxyethoxy)methyl]-4'-(4-methyl-2-oxazolyl)[1,1'-biphenyl]-2-sulfonamide To a solution of compound B from Example 1 (320 mg, 0.83 mmol) and compound A (397 mg, 1.67 mmol) in 7.5 mL of toluene and 6 mL of 95% ethanol under argon, tetrakis(triphenylphosphine)palladium(O) (96 mg, 0.083 mmol) was added, followed by 4.5 mL of 2M aqueous sodium carbonate. The reaction mixture was heated at 75° C. for 4 hours, cooled and diluted with 50 mL of ethyl acetate. The organic liquid was separated, washed with 10 mL water and 10 mL brine, dried and concentrated. The residue was chromatographed on silica gel using 2:1 Hexane/ethyl acetate to afford compound B (300 mg, 72%) as a colorless gum.

C. N-(3,4-Dimethyl-5-isoxazolyl)-4'-(4-methyl-2-oxazolyl)[1,1'-biphenyl]-2-sulfonamide To a solution of compound B (300 mg, 0.60 mmol) in 10 mL of 95% ethanol, 10 mL of 6N aqueous hydrochloric acid was added and refluxed for 1 hour. The reaction mixture was concentrated and the pH of the solution was adjusted to 8 using sodium bicarbonate solution. It was then acidified to pH 5 with glacial acetic acid. The mixture was extracted with 3×40 mL ethyl acetate. The organic liquid was washed with 10 mL water and 10 mL brine, dried and concentrated. The residue was chromatographed on silica gel using 100:1 dichloromethane/methanol to afford the title compound (200 mg, 81%) as a white solid.

M.p. 85°–95° C.(amorphous).

Analysis calculated for $C_{21}H_{19}N_3O_4S \cdot 0.25\ H_2O$: Calculated: C, 60.92; H, 4.75; N, 10.15; S, 7.74; Found: C, 61.15; H, 4.60; N, 9.89; S, 7.62.

EXAMPLE 8

N-(3,4-Dimethyl-5-isoxazolyl)-4'-(5-methyl-2-oxazolyl)[1,1'-biphenyl]-2-sulfonamide

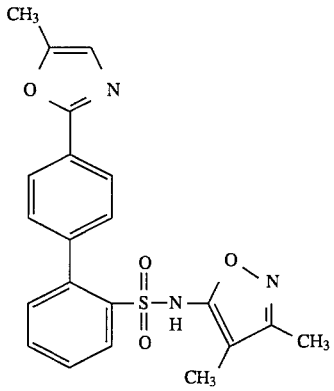

A. 2-(4-Bromophenyl)-5-methyloxazole

To 4-bromobenzoyl chloride (4.39 g, 20 mmol) in 40 mL dichloromethane at 0° C., propargylamine (1.10 g, 20 mmol) was added, followed by triethylamine (4.05 g, 40 mmol). The mixture was stirred at room temperature for 40 minutes. 150 mL ethyl acetate was added and filtered. The filtrate was washed with 2×40 mL water and 40 mL brine, dried and concentrated to give 4-Bromo-N-(2-propynyl)benzamide. 4-Bromo-N-(2-propynyl)benzamide was added into ice cooled 47 mL concentrated sulfuric acid. The reaction was stirred at 5°–10° C. for 3 hours and at room temperature overnight. The mixture was poured into 500 mL ice water, neutralized with sodium carbonate to pH 8 and extracted with 3×250 mL ethyl acetate. The combined organic extracts were washed with 200 mL water and 100 mL brine, dried and concentrated to afford compound A (4.5 g, 95%) as a light yellow solid.

M.p. 61°–63° C.

B. N-(3,4-Dimethyl-5-isoxazolyl)-N-[(2-methoxyethoxy)methyl]-4'-(5-methyl-2-oxazolyl)[1,1'-biphenyl]-2-sulfonamide To a solution of compound B from Example 1 (320 mg, 0.83 mmol) and compound A (397 mg, 1.67 mmol) in 7.5 mL of toluene and 6 mL of 95% ethanol under argon, tetrakis(triphenylphosphine)palladium(O) (96 mg, 0.083 mmol) was added, followed by 4.5 mL of 2M aqueous sodium carbonate. The reaction mixture was heated at 75° C. for 3 hours, cooled and diluted with 50 mL of ethyl acetate. The organic liquid was separated and washed with 10 mL water and 10 mL brine, dried and concentrated. The residue was chromatographed on silica gel using 2:1 Hexane/ethyl acetate to afford compound B (298 mg, 72%) as a colorless gum.

C. N-(3,4-Dimethyl-5-isoxazolyl)-4'-(5-methyl-2-oxazolyl)[1,1'-biphenyl]-2-sulfonamide To a solution of compound B (298 mg, 0.60 mmol) in 10 mL of 95% ethanol, 10 mL of 6N aqueous hydrochloric acid was added and refluxed for 1 hour. The reaction mixture was concentrated and the pH of the solution was adjusted to 8 using sodium bicarbonate solution. It was then acidified to pH 5 with glacial acetic acid. The mixture was extracted with 3×40 mL ethyl acetate. The organic liquid was washed with 10 mL water and 10 mL brine, dried and concentrated. The residue was chromatographed on silica gel using 100:1 dichloromethane/methanol to afford the title compound (147 mg, 60%) as an off-white solid.

M.p. 90°–100° C. (amorphous).

Analysis calculated for $C_{21}H_{19}N_3O_4S$: Calculated: C, 61.60; H, 4.68; N, 10.26; S, 7.83; Found: C, 61.39; H, 4.11; N, 10.03; S, 7.61.

EXAMPLE 9

N-(3,4-Dimethyl-5-isoxazolyl)-4'-(1H-pyrazol-1-yl)[1,1'-biphenyl]-2-sulfonamide

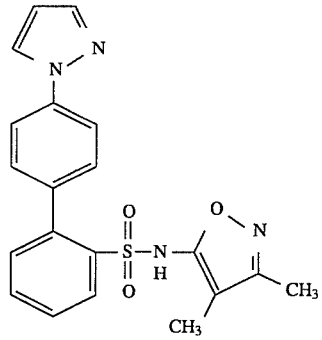

A. 1-(4-Bromophenyl)-1H-pyrazole

To epichlorohydrin (4 g, 43.23 mmol) and 4-bromophenyl hydrazine hydrochloride (19.32 g, 86.46 mmol) in 20 mL 60% ethanol, triethylamine (8.75 g, 12.05 mmol) was added dropwise. The mixture was warmed slowly and then refluxed for 1 hour. The solvent was evaporated, and the residue was heated at 170° C. for 30 minutes and at 200° C. for a further 10 minutes. 150 mL water was added, and the mixture was extracted with 3×200 mL ethyl acetate. The combined organic liquid was washed with 50 mL brine, dried and concentrated. The residue was chromatographed on silica gel using 40:1 Hexane/ethyl acetate to afford compound A (2.92 g, 30%) which was crystallized from hexane to give yellow needles.

M.p. 72°–74° C.

B. N-(3,4-Dimethyl-5-isoxazolyl)-N-[(2-methoxyethoxy)methyl]-4'-(1H-pyrazol-1-yl)[1,1'-biphenyl]-2-sulfonamide To a solution of compound B from Example 1 (320 mg, 0.83 mmol) and compound A (372 mg, 1.67 mmol) in 7.5 mL of toluene and 6 mL of 95% ethanol under argon, tetrakis(triphenylphosphine)palladium(O) (96 mg, 0.083 mmol) was added, followed by 4.5 mL of 2M aqueous sodium carbonate. The reaction mixture was heated at 75° C. for 2.5 hour, cooled and diluted with 50 mL of ethyl acetate. The organic liquid was separated, washed with 10 mL water and 10 mL brine, dried and concentrated. The residue was chromatographed on silica gel using 2.5:1 Hexane/ethyl acetate to afford compound B (280 mg, 70%) as a colorless gum.

C. N-(3,4-Dimethyl-5-isoxazolyl)-4'-(1H-pyrazol-1-yl)[1,1'-biphenyl]-2-sulfonamide To a solution of compound B (280 mg, 0.58 mmol) in 10 mL of 95% ethanol, 10 mL of 6N aqueous hydrochloric acid was added and refluxed for 1 hour. The reaction mixture was concentrated and the pH of the solution was adjusted to 8 using sodium bicarbonate solution. It was then acidified to pH 5 with glacial acetic acid. The mixture was extracted with 3×40 mL ethyl acetate. The organic liquid was washed with 10 mL water and 10 mL brine, dried and concentrated. The residue was chromatographed on silica gel using 100:0.8 dichloromethane/methanol to afford the title compound (161 mg, 70%) as an off-white solid.

M.p. 88°–98° C.(amorphous).

Analysis calculated for $C_{20}H_{18}N_4O_3S \cdot 0.12H_2O$: Calculated: C, 60.56; H, 4.64; N, 14.12; S, 8.08; Found: C, 61.26; H, 4.52; N, 13.96; S, 8.06.

EXAMPLE 10

N-(3,4-Dimethyl-5-isoxazolyl)-4'-[1-[(2-methoxyethoxy)methyl]-1H-imidazol-2-yl][1,1'-biphenyl]-2-sulfonamide

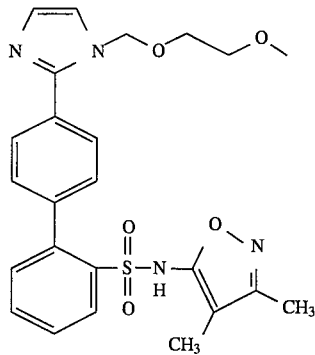

A. 2-(4-Bromophenyl)-1H-imidazole

To 4-Bromobenzaldehyde (9.25 g, 50 mmol) and glyoxal (40% wt. aqueous solution, 11.6 mL, 80 mmol) in 20 mL methanol, 60 mL 30% aqueous ammonium hydroxide was added dropwise. The mixture was stirred at room temperature overnight. The solvent was evaporated under vacuum. The residue was made slightly alkaline by the addition of aqueous sodium hydroxide, and extracted with 3×300 mL ethyl acetate. The combined organic extracts were dried and concentrated. The residue was dissolved in 100 mL methanol and filtered. The filtrate was concentrated and the residue was triturated with 20 mL ethyl ether to give compound A as a brown solid as (1.8 g, 16%).

B. 2-(4-Bromophenyl)-1-[(2-methoxyethoxy)methyl]-1H-imidazole

To compound A (400 mg, 1.79 mmol) in 18 mL tetrahydrofuran, sodium hydride (60% in mineral oil, 86 mg, 2.15 mmol) was added. The mixture was stirred at room temperature for 10 minutes. Methoxyethoxymethyl chloride (335 mg, 2.59 mmol) was added dropwise. The reaction was stirred at room temperature for 2 hours, and concentrated. 100 mL ethyl acetate was added and the organic liquid was washed with 20 mL water and 10 mL brine, dried and concentrated. The residue was chromatographed on silica gel using 100: 400:1 Hexane/ethyl acetate/triethylamine to afford compound B (390 mg, 70%).

C. N-(3,4-Dimethyl-5-isoxazolyl)-N-[(2-methoxyethoxy)methyl]-4'-[1-[(2-methoxyethoxy)methyl]-1H-imidazol-2-yl][1,1'-biphenyl]-2-sulfonamide To a solution of compound B from Example 1 (722 mg, 1.88 mmol) and compound B above (390 mg, 1.25 mmol) in 11.25 mL of toluene and 9 mL of 95% ethanol under argon, tetrakis(triphenylphosphine)palladium(O) (145 mg, 0.125 mmol) was added, followed by 6.75 mL of 2M aqueous sodium carbonate. The reaction mixture was heated at 75° C. for 3 hours, cooled and diluted with 75 mL of ethyl acetate. The organic liquid was separated, washed with 15 mL water and 15 mL brine, dried and concentrated. The residue was chromatographed on silica gel using 100:0.2 ethyl acetate/triethylamine to afford compound C (400 mg, 56%) as a colorless gum.

D. N-(3,4-Dimethyl-5-isoxazolyl)-4'-[1-[(2-methoxyethoxy)methyl]-1H-imidazole-2-yl][1,1'-biphenyl]2-sulfonamide To a solution of compound C (400 mg, 0.70 mmol) in 12 mL of 95% ethanol, 12 mL of 6N aqueous hydrochloric acid was added and refluxed for 1 hour. The reaction mixture was concentrated and the pH of the solution was adjusted to 8 using sodium bicarbonate solution. It was then acidified to pH 5 with glacial acetic acid. 200 mL ethyl acetate was added, and the organic liquid was washed with 20 mL water and 20 mL brine, dried and concentrated. The residue was chromatographed on silica gel using 100:4:0.2 dichloromethane/methanol/ammonium hydroxide to afford the title compound (210 mg, 62%), which was crystallized from ethyl acetate/Hexane to provide white crystals.

M.p. 81°–84° C.

Analysis calculated for $C_{24}H_{26}N_4O_5S \cdot 0.24\,H_2O$: Calc'd: C, 59.20; H, 5.48; N, 11.51; S, 6.58; Found: C, 59.25; H, 5.42; N, 11.46; S, 6.39.

EXAMPLE 11

N-3,4-Dimethyl-5-isoxazolyl)-4'-[1-[(2-hydroxyethoxy)methyl]-1H-imidazol -2-yl][1,1'-biphenyl]-2-sulfonamide

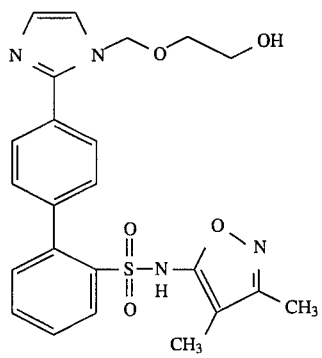

A. N-(3,4-Dimethyl-5-isoxazolyl)-4'-[1-[(2-hydroxyethoxy)methyl]-1H-imidazol-2-yl][1,1'-biphenyl]-2-sulfonamide To the title compound of Example 10 (120 mg, 0.25 mmol) in 2.5 mL dichloromethane at 0° C., boron tribromide (1M solution in dichloromethane, 0.37 mL, 0.37 mmol) was added dropwise. The reaction mixture was stirred at 0°–3° C. for 45 minutes. 5 mL saturated aqueous sodium bicarbonate was added and stirred for 10 minutes. The mixture was then acidified to pH 5 with glacial acetic acid and extracted with 3×40 ml 100:5 dichloromethane/methanol. The combined organic extracts were dried and concentrated. The residue was purified by preparative HPLC on a 30×500 mm ODS S10 column using 62% solvent A (10% methanol, 90% water, 0.1% trifluoroacetic acid) and 38% solvent B (90% methanol, 10% water, 0.1% tetrahydrofuran) to provide the title compound (80 mg, 69%) as a white solid.

M.p. 93°–103° C.

Analysis calculated for $C_{23}H_{24}N_4O_5S \cdot 0.75\ H_2O$: Calculated: C, 57.31; H, 5.33; N, 11.62; S, 6.65; Found: C, 57.61; H, 5.04; N, 11.33; S, 6.55.

EXAMPLE 12

N-(3,4-Dimethyl-5-isoxazolyl)-4'-(1-methyl-1H-imidazol-2-yl)[1,1'-biphenyl]-2-sulfonamide, lithium salt

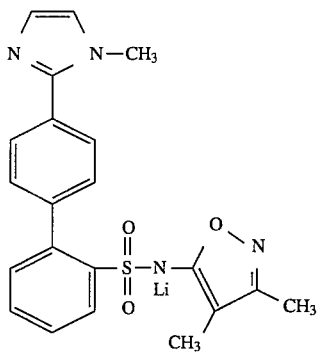

A. 2-(4-Bromophenyl)-1-methyl-1H-imidazole

To compound A from Example 10 (700 mg, 3.14 mmol) in 7.8 mL tetrahydrofuran and 7.8 mL dimethylformamide, sodium hydride (60% in mineral oil, 151 mg, 3.77 mmol) was added. The mixture was stirred at room temperature for 10 minutes. Iodomethane (891 mg, 6.28 mmol) was added dropwise. The reaction mixture was stirred at room temperature for 1 hour, and concentrated. 100 mL ethyl acetate was added and the organic liquid was washed with 20 mL water and 20 mL brine, dried and concentrated. The residue was chromatographed on silica gel using 100:1:0.1 dichloromethane/methanol/ammonium hydroxide to afford compound A (500 mg, 67%).

B. N-(3,4-Dimethyl-5-isoxazolyl)-N-[(2-methoxyethoxy)methyl]-4'-(1-methyl-1H-imidazole-2-yl)[1,1'-biphenyl]-2-sulfonamide To a solution of compound B from Example 1 (320 mg, 0.83 mmol) and compound A (395 mg, 1.67 mmol) in 7.5 mL of toluene and 6 mL of 95% ethanol under argon, tetrakis (triphenylphosphine) palladium(O) (96 mg, 0.083 mmol) was added, followed by 4.5 mL of 2M aqueous sodium carbonate. The reaction mixture was heated at 75° C. for 3 hours, cooled and diluted with 50 mL of ethyl acetate. The organic liquid was separated and washed with 10 mL water and 10 mL brine, dried and concentrated. The residue was chromatographed on silica gel using 100:1.5:0.1 dichloromethane/methanol/ammonium bicarbonate to afford compound A (254 mg, 61%) as a colorless gum.

C. N-(3,4-Dimethyl-5-isoxazolyl)-4'-(1-methyl-1H-imidazol-2-yl)[1,1'-biphenyl]-2-sulfonamide, lithium salt To a solution of compound B (250 mg, 0.50 mmol) in 9 mL of 95% ethanol, 9 mL of 6N aqueous hydrochloric acid was added and refluxed for 1 hour. The reaction mixture was concentrated and the pH of the solution was adjusted to 8 using sodium bicarbonate solution. It was then acidified to pH 5 with glacial acetic acid. The mixture was extracted with 200 mL ethyl acetate and the organic layer was washed with 20 mL water and 20 mL brine, dried and concentrated. The residue was chromatographed on silica gel using 100:6:0.3 dichloromethane/methanol/ammonium bicarbonate to afford N-(3,4-Dimethyl-5-isoxazolyl)-4'-(1-methyl-1H-imidazol-2-1)[1,1'-biphenyl]-2-sulfonamide (189 mg, 92%), which was dissolved in 1N lithium hydroxide, added on to a HP-20 column and eluted with water and then 10:3 water/methanol to provide the title compound as a white solid.

M.p. >200° C. dec.

Analysis calculated for $C_{21}H_{19}N_4O_3SLi \cdot 2.75H_2O$: Calculated: C, 54.37; H, 5.32; N, 12.08; S, 6.91; Found: C, 54.58; H, 5.05; N, 11.87; S, 6.80.

EXAMPLE 13

N-(3,4-Dimethyl-5-isoxazolyl)-4'-(1H-imidazol-2-yl)[1,1'-biphenyl]-2-sulfonamide, lithium salt

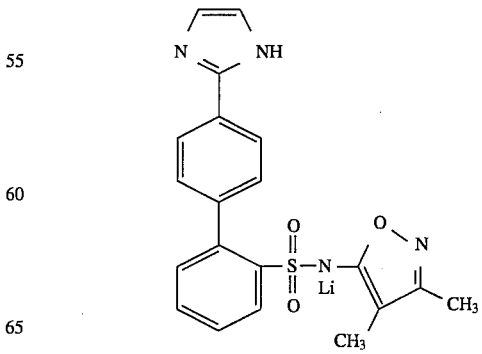

A. 2-(4-Bromophenyl)-1H-imidazole-1-carboxylic acid, 1,1-dimethylethyl ester

To compound A from Example 10 (446 mg, 2 mmol) in 20 mL acetonitrile, di-t-butyl dicarbonate (524 mg, 2.4 mmol) and 4-dimethylaminopyridine (24.4 mg, 0.2 mmol) were added. The reaction mixture was stirred at room temperature overnight and concentrated. The residue was chromatographed on silica gel using 6:1 hexane/ethyl acetate to afford compound A (500 mg, 77%) as a light yellow oil.

B. 4'-[1-[(1,1-Dimethylethoxy)carbonyl]-1H-imidazol-2-yl]-N-(3,4-Dimethyl-5-isoxazolyl)-N-[(2-methoxyethoxy)methyl][1,1'-biphenyl]-2-sulfonamide To a solution of compound B from Example 1 (496 mg, 1.29 mmol) and compound A (500 mg, 1.55 mmol) in 11.25 mL of toluene and 9 mL of 95% ethanol under argon, tetrakis(triphenylphosphine)palladium(O) (149 mg, 0.29 mmol) was added, followed by 6.75 mL of 2M aqueous sodium carbonate. The reaction mixture was heated at 75° C. for 3 hours, cooled and diluted with 75 mL of ethyl acetate. The organic liquid was separated and washed with 15 mL water and 15 mL brine, dried and concentrated. The residue was chromatographed on silica gel using 40:60:0.2 hexane/ethyl acetate/triethylamine to afford compound B (380 mg, 51%) as a colorless gum.

C. N-(3,4-Dimethyl-5-isoxazolyl)-4'-(1H-imidazole-2-yl)[1,1'-biphenyl]-2-sulfonamide, lithium salt To a solution of compound B (380 mg, 0.65 mmol) in 12 mL of 95% ethanol, 12 mL of 6N aqueous hydrochloric acid was added and refluxed for 1 hour and 45 minutes. The reaction mixture was concentrated and the pH of the solution was adjusted to 8 using sodium bicarbonate solution. It was then acidified to pH 5 with glacial acetic acid, extracted with 3×80 mL 100:5 dichloromethane/methanol. The organic extracts were dried and concentrated. The residue was dissolved in 1N lithium hydroxide and chromatographed on HP-20 column eluted with water and then 10:2 water/methanol to provide the title compound as a white solid (180 mg, 69%).

M.p. >220° C. dec.

Analysis calculated for $C_{20}H_{17}N_4O_3SLi \cdot 2.06H_2O$: Calculated: C, 54.91; H, 4.87; N, 12.81; S, 7.33; Found: C, 54.99; H, 4.78; N, 12.73; S, 6.95.

EXAMPLE 14

N-(3,4-Dimethyl-5-isoxazolyl)-4'-(5-methyl-4-oxazolyl)[1,1'-biphenyl]-2-sulfonamide

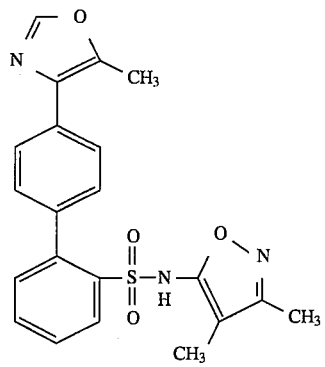

A. 4-(4-Bromophenyl)-5-methyloxazole

To 4'-Bromopropiophenone (3.52 g, 16.5 mmol) and formamide (10.81 g, 240 mmol) at 50° C., bromine (2.40 g, 15 mmol) was added dropwise over 10 minutes. The reaction mixture was heated from 50° C. to 130° C. over 20 minutes and then heated at 130° C. for 4 hours. After cooling, 150 mL ethyl acetate was added and the liquid was washed with 2×20 mL water and 20 mL brine, dried and concentrated. The residue was chromatographed on silica gel using 40:1 Hexane/ethyl acetane to afford compound A (1.59 g, 45%).

B. N-(3,4-Dimethyl-5-isoxazolyl)-N-[(2-methoxyethoxy)methyl]-4'-(5-methyl-4-oxazolyl)[1,'-biphenyl]-2-sulfonamide To a solution of compound B from Example 1 (384 mg, 1.0 mmol) and compound A (408 mg, 1.7 mmol) in 9 mL of toluene and 7.2 mL of 95% ethanol under argon, tetrakis(triphenylphosphine)palladium(O) (116 mg, 0.10 mmol) was added, followed by 5.4 mL of 2M aqueous sodium carbonate. The reaction mixture was heated at 75° C. for 3 hours, cooled and diluted with 60 mL of ethyl acetate. The organic liquid was separated and washed with 15 mL water and 15 mL brine, dried and concentrated. The residue was chromatographed on silica gel using 2.5:1 Hexane/ethyl acetate to afford compound B (317 mg, 64%) as a colorless gum.

C. N-(3,4-Dimethyl-5-isoxazolyl)-4'-(5-methyl-4-oxazolyl)[1,1'-biphenyl]-2-sulfonamide To a solution of compound B (300 mg, 0.60 mmol) in 10 mL of 95% ethanol, 10 mL of 6N aqueous hydrochloric acid was added and refluxed for 1 hour. The reaction mixture was concentrated and the pH of the solution was adjusted to 8 using sodium bicarbonate solution. It was then acidified to pH 5 with glacial acetic acid. The mixture was extracted with 3×40 mL ethyl acetate and the organic extracts were washed with 10 mL water and 10 mL brine, dried and concentrated. The residue was purified by preparative HPLC on a 30×500 mm ODS S10 column using 30% solvent A (10% methanol, 90% water, 0.1% trifluoroacetic acid) and 70% solvent B (90% methanol, 10% water, 0.1% tetrahydrofuran) to provide the title compound (150 mg, 61%) as a white solid.

M.p. 86°–96° C.(amorphous).

Analysis calculated for $C_{21}H_{19}N_3O_4S \cdot 0.16H_2O$: Calculated: C, 61.17; H, 4.72; N, 10.19; S, 7.77; Found: C, 61.20; H, 4.35; N, 10.16; S, 7.58.

EXAMPLE 15

N-(3,4-Dimethyl-5-isoxazolyl)-4'-(1H-imidazol-1-ylmethyl)[1,1'-biphenyl]-2-sulfonamide

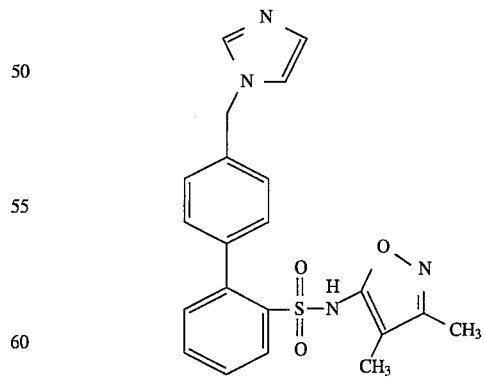

A. N-(3,4-Dimethyl-5-isoxazolyl)-2-bromo-benzenesulfonamide

To a solution of 3.0 g (11.74 mmol) of 2-bromobenzenesulfonyl chloride in 10 mL of pyridine was added 1.32 g (11.74 mmol) of 3,4-dimethyl-5-isoxazolamine. The mixture was stirred at room temperature under argon overnight, added to 150 mL of ice water and filtered. The filtrate was acidified to pH 2 using 6N aqueous hydrochloric acid and the grey solid was filtered and dried. The solid was crystallized from methanol/water to afford 4.0 g (>100%) of compound A as tan crystalline needles (m.p. 125°–126° C.; $R_f$=0.51 (10% methanol/dichloromethane)).

B.  2-Bromo-N-(3,4-dimethyl-5-isoxazolyl)-N'-(methoxyethoxymethyl)benzenesulfonamide To a solution of 1.1 g (3.33 mmol) of compound A in 15 mL of THF at room temperature under argon was added 0.19 g (4.8 mmol) of sodium hydride (60% suspension in mineral oil ) in portions, and the solution was stirred at room temperature for 10 minutes. Methoxyethoxymethyl chloride (0.55 g, 4.4 mmol ) was then added and the solution was stirred overnight. The mixture was concentrated and diluted with 30 mL of water, and extracted with 40 mL of ethyl acetate. The combined organic extracts were washed with 50 mL of brine, dried and evaporated to provide 1.2 g (87%) of compound B as a brown gum.

C.  N-(3,4-Dimethyl-5-isoxazolyl)-N-[(2-methoxyethoxy)methyl]-4'-methyl[1,1'-biphenyl]-2-sulfonamide To a solution of compound B, 4-methylbenzeneboronic acid (4.76 g, 35 mmol) in 250 mL of toluene and 200 mL of 95% ethanol under argon, tetrakis(triphenylphosphine)palladium(O) (2.43 g, 2.1 mmol) was added, followed by 150 mL of 2M aqueous sodium carbonate. The reaction mixture was heated at 80° C. for 2.5 hours, cooled and diluted with 300 mL of ethyl acetate. The organic liquid was separated and washed with 200 mL water and 200 ml of brine, dried and concentrated. The residue was chromatographed on silica gel using 5:1 hexane/ethyl acetate to afford compound C (9.0 g, 60%) as a colorless gum.

$R_f$=0.74, silica gel, 1:1 Hexane/ethyl acetate.

D.  4'-(Bromomethyl)-N-(3,4-dimethyl-5-isoxazolyl)-N-[(2-methoxyethoxy)methyl][1,1'-biphenyl]-2-sulfonamide To compound C (7.7 g, 17.89 mmol) in 180 mL carbon tetrachloride, n-bromosuccinimide (4.14 g, 23.25 mmol) and benzoyl peroxide (385 mg, 1.59 mmol) were added. The reaction was refluxed for 1.5 hours. After cooling, the reaction mixture was diluted with 200 mL dichloromethane, washed with 2×100 ml water and 100 mL brine, dried and concentrated. The residue was chromatographed on silica gel eluting with 4:1 hexane/ethyl acetate to provide compound D (3.64 g, 40%) as a colorless gum.

$R_f$=0.38, silica gel, 2:1 Hexane/ethyl acetate.

E.  N-(3,4-Dimethyl-5-isoxazolyl)-4'-(1H-imidazol-1-ylmethyl)-N-[(2-methoxyethoxy)-methyl][1,1'-biphenyl]-2-sulfonamide To compound D (400 mg, 0.79 mmol) and imidazole (133 mg, 1.95 mmol) potassium carbonate ($K_2CO_3$) (326 mg, 2.36 mmol) was added. The reaction was stirred at room temperature for 10 hours and then at 50° C. for 1 hour. The mixture was diluted with 50 mL ethyl acetate, washed with 10 mL water and 10 mL brine, dried and concentrated. The residue was chromatographed on silica gel using 100:1.5 dichloromethane/methanol to afford compound E (220 mg, 56%) as a colorless gum.

$R_f$=0.52, silica gel, 10:1 trichloromethane/methanol.

F.  N-(3,4-Dimethyl-5-isoxazolyl)-4'-(1H-imidazol-1-ylmethyl)[1,1'-biphenyl]-2-sulfonamide To a solution of compound E (220 mg, 0.44 mmol) in 6 mL of 95% ethanol, 6 mL of 6N aqueous HCl was added. The reaction was refluxed for 2 hours, cooled and concentrated. The reaction mixture was neutralized with saturated aqueous sodium bicarbonate ($NaHCO_3$), and then acidified to pH <5 with acetic acid. Filtration of the mixture provided a white solid (91 mg, 50%) which was dissolved in 1N HCl and concentrated under vacuum to give the hydrochloride salt of the title compound as a white solid (m.p. 150° C. dec.)

$R_f$=0.27, silica gel, 10:1 dichloromethane/methanol.

Analysis calculated for $C_{21}H_{20}N_4O_3S$ 1.1 $H_2O$ . 0.8 HCl: C, 55.02; H, 5.28; N, 12.22; S, 6.99; Cl, 6.19. Found: C, 54.67; H, 4.88; N, 11.97; S, 6.93; Cl, 6.30.

EXAMPLE 16

N-(3,4-Dimethyl-5-isoxazolyl)-4'-(3-isoxazolyl)[1,1'-biphenyl]-2-sulfonamide

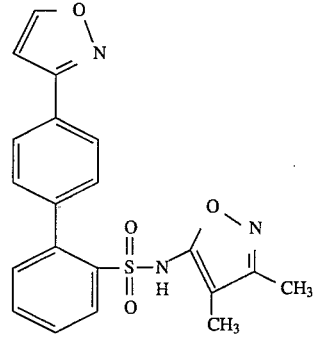

A. 4-Bromo-N-hydroxybenzenecarboximidoyl bromide

To a 0.5M solution of hydrochloric acid in dimethylformamide, 8.5 g (42.5 mmol) of 4-Bromobenzaldehyde oxime was added and cooled to 5° C. 13 g of oxone was then added in portions. The mixture was slowly warmed to room temperature and stirred for 8 hours. The reaction mixture was poured into 300 mL of cold water and extracted with 2×150 mL of ether. The combined organic extracts were washed once with 150 mL of 0.5N aqueous hydrochloric acid and brine (150 mL), dried and evaporated to provide 7.9 g (79%) of compound A.

B. 5-(Acetyloxy)-3-(4-bromophenyl)-4,5-dihydroisoxazole

A mixture of 4.0 g (17.06 mmol) of compound A, 7.34 g (85.3 mmol) of vinyl acetate and 1.9 g (18.76 mmol) of triethylamine in 50 mL of toluene was stirred at 75° C. for 2 hours. The mixture was cooled and added to 150 mL of water. The organic layer was separated and the aqueous layer was extracted with 2×50 mL of ethyl acetate. The combined organic extracts were washed once with 100 mL of brine, dried and evaporated. The residue was crystallized from Hexanes/ethyl acetate to afford 3.6 g (74%) of compound B as a white solid.

C. 3-(4-Bromophenyl)isoxazole

To a solution of 3.0 g (10.56 mmol) of compound B in 100 mL of absolute ethanol, 5 mL of 6N aqueous hydrochloric acid was added and the solution was refluxed for 3 hours. The mixture was concentrated to about 10 mL and the solution was neutralized using aqueous sodium bicarbonate. The resulting mixture was extracted with 2×50 mL of ether. The combined organic extracts were washed once with 100 mL of brine, dried and evaporated. The residue was chromatographed on 100 g of silica gel using Hexanes/ethyl acetate 9:1 to afford 1.6 g (68%) of compound C as a white solid.

D.  N-(3,4-Dimethyl-5-isoxazolyl)-N-[(2-methoxyethoxy)methyl]-4'-(3-isoxazolyl)[1,1'-biphenyl]-2-sulfonamide To a solution of 0.45 g (1.17 mmol) of compound B from Example 1 and 0.058 g (0.05 mmol) of tetrakis(triphenylphosphine)palladium(O) in 20 mL of toluene under argon, 12 mL of 2M aqueous sodium carbonate was added followed by 0.315 g (1.4 mmol) of compound C in 12 mL of 95% ethanol. The mixture was refluxed for 2 hours, diluted with 100 mL of water and extracted with 3×50 mL of ethyl acetate. The combined organic extracts were washed once with 100 mL of brine, dried and evaporated. The residue was chromatographed on 50 g of silica gel using Hexanes/ethyl acetate 2:1 to afford 0.27 g (56%) of compound D as a colorless gum.

E. N-(3,4-Dimethyl-5-isoxazolyl)-4'-(3-isoxazolyl)[1,1'-biphenyl]-2-sulfonamide

To a solution of 0.26 g (0.54 mmol) of compound D in 10 mL of 95% ethanol, 10 mL of 6N aqueous hydrochloric acid was added and refluxed for 1 hour. The mixture was then concentrated, diluted with 50 mL of water and extracted with 3×25 ml of ethyl acetate. The combined organic extracts were washed once with water, dried and evaporated (0.21 g). This material was purified by reverse phase preparative HPLC on a 30×500 mm ODS S10 column using 67% solvent B (90% methanol, 10% water, 0.1% trifluoroacetic acid) and 33% solvent A (10% methanol, 90% water, 0.1% trifluoroacetic acid). The appropriate fractions were collected, neutralized with aqueous sodium bicarbonate to pH 7 and concentrated to 10 mL. The solution was then acidified to pH 4 using glacial acetic acid and the white solid was filtered and dried to provide 0.13 g (61%) of the title compound.

M.p. 85°–90° C.

Analysis Calculated for $C_{20}H_{17}N_3O_4S \cdot 0.26\ H_2O$: Calculated: C,60.04; H,4.41; N,10.50; S,8.01; Found: C,60.04; H,4.30; N,10.50; S,8.15.

EXAMPLE 17

N-(3,4-Dimethyl-5-isoxazoyl)-4'-(2-oxazolylmethyl) [1,1'-biphenyl]-2-sulfonamide

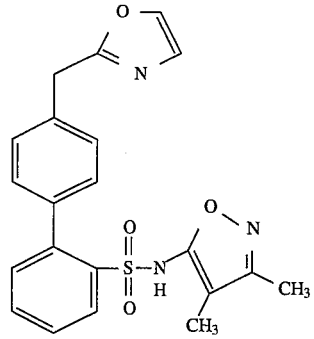

A. 4-Bromobenzeneacetamide

To a solution of 6 g (27.9 mmol) of 4-bromophenylacetic acid in 200 mL of dichloromethane under argon, 14 mL of 2M solution of oxalyl chloride in dichloromethane was added. Then four drops of dimethylformamide was added and the mixture was stirred at room temperature for 1 hour. The solution was evaporated and dried in vacuo. The residue was dissolved in 150 mL of methanol, and 30 mL of 28% aqueous ammonium hydroxide was added to the mixture. The solution was stirred at room temperature overnight and then diluted with 150 mL of water. The resulting white solid was filtered, washed with water and dried to afford 5.1 g (85%) of compound A.

B. 2-[(4-Bromophenyl)methyl]oxazole

A mixture of compound A (2 g, 9.34 mmol) and vinylene carbonate (0.9 g, 10.45 mmol) in 6 g of polyphosphoric acid was heated at 170° C. for 3 hours. The residue was added to 100 mL of water and extracted with 2×100 mL of ethyl acetate. The combined organic extracts were washed once with water, dried and evaporated. The residue was chromatographed on 200 mL of silica gel using Hexanes/ethyl acetate 2:1 to provide 1.12 g (50%) of compound C as a white solid.

C. N-(3,4-Dimethyl-5-isoxazolyl)-N-[(2-methoxyethoxy)methyl]-4'-(2-oxazolylmethyl)[1,1'-biphenyl]-2-sulfonamide To a solution of 0.6 g (1.56 mmol) of compound B from Example 1 and 0.092 g (0.08 mmol) of tetrakis(triphenylphosphine)palladium(O) in 30 mL of toluene under argon, 15 mL of 2M aqueous sodium carbonate was added followed by 0.45 g (1.87 mmol) of compound B above in 15 mL of 95% ethanol. The mixture was refluxed for 2 hours, diluted with 100 mL of water and extracted with 3×50 mL of ethyl acetate. The combined organic extracts were washed once with 100 mL of brine, dried and evaporated. The residue was chromatographed on 200 mL of silica gel using Hexanes/ethyl acetate 2:1 to afford 0.72 g (93%) of compound C as a colorless gum.

D. N-(3,4-Dimethyl-5-isoxazolyl)-4'-(2-oxazolylmethyl)[1,1'-biphenyl]-2-sulfonamide To a solution of 0.7 g (1.41 mmol) of compound C in 15 mL of 95% ethanol, 15 mL of 6N aqueous hydrochloric acid was added and refluxed for 1 hour. The mixture was then concentrated, diluted with 250 mL of water and extracted with 3×50 ml of ethyl acetate. The combined organic extracts were washed once with water, dried and evaporated to provide 0.41 g of a colorless gum. The residue was purified by reverse phase preparative HPLC on a 30×500 mm ODS S10 column using 67% solvent B (90% methanol, 10% water, 0.1% trifluoroacetic acid) and 23% solvent A (10% methanol, 90% water, 0.1% trifluoroacetic acid). The appropriate fractions were collected and neutralized with aqueous sodium bicarbonate to pH 7 and concentrated to 10 mL. The solution was then acidified to pH 4 using dilute hydrochloric acid and the resulting white solid was filtered and dried to provide 0.098 g (17%) of the title compound.

M.p. 65°–70° C.

$^1$H NMR (CDCl$_3$): δ1.80 (s,3H), 2.11 (s, 3H), 4.16 (s,2H), 7.04 (s, 1H), 7.27–8.02 (m, 10H). $^{13}$C NMR (CDCl$_3$): δ6.99, 11.20, 34.67, 108.10, 127.54, 128.32, 128.92, 129.47, 130.82, 133.15, 133.44, 135.95, 137.91, 138.51, 139.37, 141.25, 154.69, 162.27, 163.42.

EXAMPLE 18

N-(3,4-Dimethyl-5-isoxazolyl)-4'-(5-isoxazolyl)[1,1'-biphenyl]-2-sulfonamide

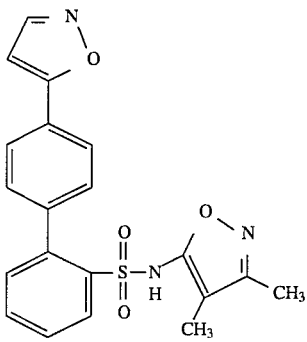

A. 1-(4-Bromophenyl)-3-(dimethylamino)-2-propen-1-one

A solution of 7.0 g (35.2 mmol) of 4-bromoacetophenone in 7 mL of N,N-dimethylformamide diethyl acetal was refluxed for 20 hours. The solution was then diluted with 100 mL ether and cooled to 0° C. The yellow crystalline solid was filtered and dried to provide compound A (6.85 g, 77%).

B. 5-(4-Bromophenyl)isoxazole

To a solution of 6.2 g (24.4 mmol) of compound A in 70 mL of methanol at 0° C. was added a solution of 3.31 g (29.27 mmol) of hydroxylamine-0sulfonic acid in 20 mL of methanol over a period of 3 minutes. After stirring at room temperature for 1 hour, the reaction mixture was poured into a mixture of cold saturated sodium bicarbonate solution (200 mL) and ice-water (200 mL). The resulting mixture deposited 5.1 g of a light yellow solid. Recrystallization of this material in Hexane/ethyl acetate then provided 3.12 g (57%) of compound B as an off-white solid.

C. N-(3,4-Dimethyl-5-isoxazolyl)-N-[(2-methoxyethoxy)methyl]-4'-(5-isoxazolyl)[1,1'-biphenyl]-2-sulfonamide To a solution of 0.56 g (1.46 mmol) of compound 1 from Example 1 and 0.081 g (0.07 mmol) of tetrakis(triphenylphosphine)palladium(O) in 25 mL of toluene under argon, 15 mL of 2M aqueous sodium carbonate was added followed by 0.49 g (2.18 mmol) of compound B in 15 mL of 95% ethanol. The mixture was refluxed for 2 hours, diluted with 100 mL of water and extracted with 3×50 mL of ethyl acetate. The combined organic extracts were washed once with 100 mL of brine, dried and evaporated. The residue was chromatographed on 50 g of silica gel using Hexanes/ethyl acetate 2:1 to afford 0.26 g (37%) of compound C as a colorless gum.

D. N-(3,4-Dimethyl-5-isoxazolyl)-4'-(5-isoxazolyl)[1,1'-biphenyl]-2-sulfonamide

To a solution of 0.25 g (0.52 mmol) of compound C in 10 mL of 95% ethanol, 10 mL of 6N aqueous hydrochloric acid was added and refluxed for 1 hour. The mixture was then concentrated, diluted with 100 mL of water and extracted with 3×50 ml of ethyl acetate. The combined organic extracts were washed once with water, dried and evaporated (0.21 g). This material was purified by reverse phase preparative HPLC on a 30×500 mm ODS S10 column using 69% solvent B (90% methanol, 10% water, 0.1% trifluoroacetic acid) and 31% solvent A (10% methanol, 90% water, 0.1% trifluroacetic acid). The appropriate fractions were collected and neutralized with aqueous sodium bicarbonate to pH 7 and concentrated to 10 mL. The solution was acidified to pH 4 using glacial acetic acid and the white solid was filtered and dried to provide 0.11 g (53%) of the title compound.

M.p. 85°–90° C.

Analysis Calculated for $C_{20}H_{17}N_3O_4S \cdot 0.27\ H_2O$: Calculated: C,60.02; H,4.42; N,10.50; S,8.01; Found: C,60.16; H,4.24; N,10.36; S,8.17.

EXAMPLE 19

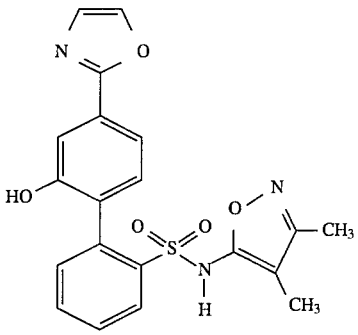

N-(3,4-Dimethyl-5-isoxazolyl)-2'-hydroxy-4'-(2-oxazolyl)-[1,1'-biphenyl]-2-sulfonamide A. 4-Bromo-3-hydroxybenzoic acid Bromine (58 g, 19 mL, 0.36 mol) in acetic acid (50 mL) was slowly added over 2 hours to a solution of 3-hydroxybenzoic acid (50 g, 0.36 mol) in acetic acid (145 mL) with stirring at 15° C. After stirring at 15° C. for an additional hour and then at ambient temperature for 17 hours, the solid formed was filtered and rinsed with acetic acid (20 mL). Drying by pulling air through the filter pack for 4 hours afforded 23.5 g (30%) of compound A.

B. 4-Bromo-3-hydroxybenzoic acid, methyl ester

Sulfuric acid (concentrated, 9.4 mL) was added to a solution of compound A (23.5 g, 0.11 mol) in methanol (350 mL). After refluxing for 19 hours, the reaction was allowed to cool to room temperature and the pH was brought to about 4 with saturated sodium bicarbonate. After evaporating the methanol, the remaining solution was transferred to a separatory funnel. Extraction with ether (2×200 mL), washing the combined organic layers with brine (50 mL), and drying over magnesium sulfate afforded 25 g of crude product after evaporation of the solvent. Recrystallization from ether/hexane afforded 13.3 g (53%) of compound B.

C. 4-Bromo-3-methoxybenzoic acid, methyl ester

Dimethyl sulfate (6.4 mL, 67 mmol) and potassium carbonate (10 g) were added to a solution of compound B (13.3 g, 57 mmol) in acetone (86 mL). After refluxing for 19 hours, the reaction was cooled, the precipitate filtered off and the filtrate evaporated in vacuo to afford 14.7 g of crude product. Flash chromatography (silica, 50 mm diameter, 10% ethyl acetate/hexane) afforded 13.9 g of compound C (100%).

D. 4-Bromo-3-methoxybenzoic acid

Potassium hydroxide (2N, 120 mL, 240 mmol) was added to a solution of compound C (19 g, 79 mmol) in methanol (570 mL). After stirring at ambient temperature for 5.5 hours, water (100 mL) was added and the methanol removed in vacuo. The remaining solution was extracted with methylene chloride and then acidified with 6N hydrochloric acid to pH 1.5. Extraction with methylene chloride (1×500 mL and 2×200 mL) afforded 17 g (93%) of compound D after evaporation of the solvent.

E. 4-Bromo-3-methoxybenzamide

A solution of compound D (17 g, 73 mmol) and dimethylformamide (0.3 mL) in thionyl chloride (18 mL, 3.5 mol) was heated at 60° C. for 2 hours. After evaporating the reaction in vacuo and azeotroping with toluene (twice), the residue was dissolved in tetrohydrofuran (30 mL) and added slowly to a vigorously stirring concentrated ammonium hydroxide solution (95 mL). The precipitate was filtered, washed with water and dried in a vacuum desiccator overnight to afford 17 g (100%) of compound E.

F. 2-(4-Bromo-3-methoxyphenyl)oxazole

Polyphosphoric acid (18 g) was added to compound E (8.5 g, 37 mmol) and the mixture was heated and stirred until it was homogeneous. Vinylene carbonate (3.2 g, 2.4 mL, 37 mmol) was added and the reaction mixture was stirred at 160° C. for 2 hours during which Lime the reaction mixture evolved gas and turned black and gummy. After cooling, water and ether were added, mixed and decanted (three times). The decanted layers were filtered through Celite® and the filtrate transferred to a separatory funnel. The organic layer was washed with water (10 mL) and 1N sodium hydroxide (30 mL), and dried over magnesium sulfate to afford crude product after evaporation of the solvent. Any solid remaining in the reaction flask and the Celite® filter pad were rinsed with dichloromethane (3×10 mL) which was then washed with in sodium hydroxide (30 mL) and dried over magnesium sulfate. The two portions of crude product totaled 3.6 g. Flash chromatography (silica, 50 mm diameter, 30% ethyl acetate/hexane) afforded 2.3 g (24%) of compound F.

M.p. 68.5°–70.5° C.

G. N-(3,4-Dimethyl-5-isoxazolyl)-2'-methoxy-N-(2-methoxyethoxymethyl)-4'-(2-oxazolyl)[1,1'-biphenyl]-2-sulfonamide A solution of compound B from Example 1 (2.3 g, 2.9 mmol) in ethanol (sparged with argon 20 minutes, 16 mL) was added to a solution of compound F (1.1 g, 4.4 mmol) in toluene (sparged with argon 20 minutes, 32 mL). To this solution was added a solution of sodium carbonate (1.0 g) in water (sparged with argon 20 min, 16 mL) followed by tetrakis(triphenylphosphine)palladium(O) (0.28 g, 0.24 mmol). After refluxing under argon for 2 hours, the solution was cooled and poured into brine (40 mL). Extraction with ethyl acetate (2×150 mL) and drying the combined organic layers over magnesium sulfate afforded 4.1 g of crude product after evaporation of the solvent. Flash chromatography (silica, 50 mm diameter, 40% ethyl acetate/hexane) afforded 0.50 g (34%) of compound G.

H. N-(3,4-Dimethyl-5-isoxazolyl)-2'-methoxy-4'-(2-oxazolyl)[1,1'-biphenyl]-2-sulfonamide A solution of compound G (0.45 g, 0.88 mmol) in ethanol (13.4 mL) and 6N hydrochloric acid (13.4 mL) was stirred at 90° C. After 3.5 hours, the ethanol was evaporated in vacuo, and the residue transferred to a separatory funnel with dichloromethane/water. Extraction with dichloromethane (2×50 mL) and drying over magnesium sulfate afforded 0.37 g (100%) of compound H after evaporation of the solvent.

I. N-(3,4-Dimethyl-5-isoxazolyl)-2'-hydroxy-4'-(2-oxazolyl)[1,1'-biphenyl]-2-sulfonamide Boron tribromide (1M in dichloromethane, 6.2 mL, 6.2 mmol) was added to a solution of compound H (0.33 g, 0.77 mmol) in methylene chloride (27 mL) with stirring at −78° C. After stirring at −78° C. for 30 minutes, the cold bath was removed. After stirring a total of 2.5 hours, the reaction mixture was transferred to a separatory funnel with dichloromethane/water. The pH was brought to 3.5 with saturated sodium bicarbonate. Extraction with dichloromethane (2×70 mL), and drying over magnesium sulfate afforded 0.68 g of crude product after evaporation of the solvent. Two flash chromatographies (silica, 25 mm diameter, 6% methanol/dichloromethane and silica, 15 mm diameter, 50% ethyl acetate/dichloromethane) afforded 60 mg (19%) of the title compound.

M.p. 111.0°–115.0° C.

Analysis calculated for $C_{20}H_{17}N_3O_5S \cdot 0.15\ C_4H_8O_2 \cdot 0.40\ H_2O$: Calculated: C, 57.29; H, 4.43; N, 9.73; S, 7.42; Found: C, 57.30; H, 4.58; N, 9.37; S, 7.18.

EXAMPLE 20

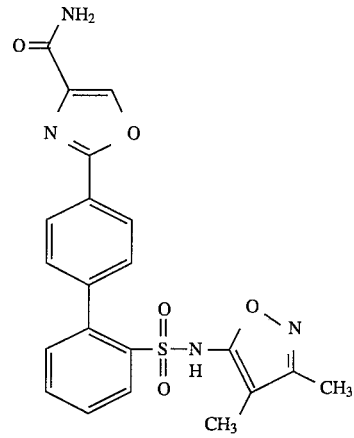

2-[2'-[[(3,4-Dimethyl-isoxazoly)amino]sulfonyl][1,1'-biphenyl]-4-yl]-4-oxazolecarboxamide A. 2-(4-Bromophenyl)-4-oxazolecarboxaldehyde A mixture of compound A from Example 7 (810 mg, 3.40 mmol) selenium dioxide (1.89 g, 17 mmol) and 6.8 mL dioxane was refluxed for 24 hours. After cooling the mixture was filtered and the filtrate was concentrated. The residue was chromatographed on silica gel using 60:1 dichloromethane/ethyl acetate to afford compound A (406 mg, 47%) as a light yellow solid.

B. N-(3,4-Dimethyl-5-isoxazolyl)-4'-(4-formyl-2-oxazolyl)-N-[(2-methoxyethoxy)methyl][1,1'-biphenyl]-2-sulfonamide To a solution of compound B from Example 1 (772 mg, 2.0 mmol), compound A (390 mg, 1.55 mmol) in 15 mL of toluene and 12 mL of 95% ethanol under argon, tetrakis(triphenylphosphine)palladium(O) (116 mg, 0.1 mmol) was added, followed by 9 mL of 2M aqueous sodium carbonate. The reaction mixture was heated at 75° C. for 1 hour, cooled and diluted with 80 mL of ethyl acetate. The organic liquid was separated, washed with 15 mL water and 15 mL brine, dried and concentrated. The residue was chromatographed on silica gel using 3:2 hexane/ethyl acetate to afford compound B (290 mg, 37%) as a colorless gum.

C. 2-[2'-[[(3,4-Dimethyl-5-isoxazoyl)[(2-methoxyethoxy)methyl]amino]sulfonyl][1,1'-biphenyl]-4-yl]-4-oxazolecarboxamide To compound B (285 mg, 0.56 mmol) above and sulfamic acid (108 mg, 1.11 mmol) in 5.6 mL tetrahydrofuran at 0° C., an ice cooled solution of sodium chlorite (101 mg, 1.11 mmol) in 5.6 mL water was added. The mixture was stirred at 0° C. for 3 minutes. 50 mL dichloromethane was added and the organic liquid was washed with 10 mL brine, dried and concentrated to give 2-[2'-[[(3,4-Dimethyl-5-isoxazolyl)

[(2-methoxyethoxy)methyl]amino]sulfonyl][1,1'-biphenyl]-4-yl]-4-oxazolecarboxylic acid.

To 2-[2'-[[(3,4-Dimethyl-5-isoxazolyl)[(2-methoxyethoxy)methyl]amino]sulfonyl][1,1'-biphenyl]-4-yl]-4-oxazolecarboxylic acid and 0.014 mL dimethylformamide in 5.6 mL dichloromethane, oxalyl chloride (2M in dichloromethane, 0.56 mL, 1.11 mmol) was added, stirred for 0.5 hours and concentrated. To this mixture, 10 mL tetrahydrofuran and 2 mL concentrated ammonium hydroxide were added. The reaction mixture was stirred at room temperature for 50 minutes and concentrated. The organic liquid was washed with 15 mL water and 15 mL brine, dried and evaporated. The residue was chromatographed on silica gel using 1:4 hexane/ethyl acetate to afford compound C (245 mg, 84% for three steps) as a colorless gum.

D. 2-[2'-[[(3,4-Dimethyl-5-isoxazolyl)amino]sulfonyl][1,1'-biphenyl]-4-yl]-4-oxazolecarboxamide To a solution of compound C (240 mg, 0.46 mmol) in 4.6 mL acetonitrile at 0° C., trimethylsilicon chloride (297 mg, 2.74 mmol) was added followed by sodium iodide (410 mg, 2.74 mmol). The mixture was stirred at room temperature for 1 hour. 5 mL water was added and extracted with 50 mL ethyl acetate. The organic liquid was washed with 5 mL saturated aqueous sodium thiosulfate and 5 mL brine, dried and concentrated. The residue was purified by preparative HPLC on a 30×500 mm ODS S10 column using 37% solvent A (10% methanol, 90% water, 0.1% trifluoroacetic acid) and 63% solvent B (90% methanol, 10% water, 0.1% tetrahydrofuran) to provide the title compound (122 mg, 61%) as a white solid.

M.p. 195° C. dec.

Analysis calculated for $C_{21}H_{18}N_4O_5S \cdot 0.23H_2O$: Calculated: C, 57.00; H, 4.20; N, 12.66; S, 7.24; Found: C, 57.01; H, 4.10; N, 12.65; S, 7.18.

EXAMPLE 21

N-(3,4-Dimethyl-5-isoxaolyl)-2'-[(formylamino)methyl]-4'-(2-oxazolyl)[1,1'-biphenyl]-2-sulfonamide

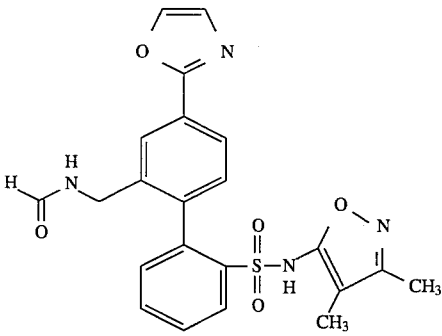

A. 4-Bromo-3-methylbenzamide

To a solution of 10 g (46.5 mmol) of 4-bromo-3-methyl benzoic acid in 200 mL of dichloromethane under argon, 30 mL of 2M solution of oxalyl chloride in dichloromethane was added. Four drops of dimethylformamide was then added and the mixture was stirred at room temperature for 1 hour. The solution was evaporated and dried in vacuo. The residue was dissolved in 100 mL of methanol, and 25 mL of 28% aqueous ammonium hydroxide was added to the mixture. The solution was stirred at room temperature for 3 hours, and then diluted with 500 mL of water. The resulting white solid was filtered, washed with water and dried to afford 8.9 g (89%) of compound A.

B. 2-(4-Bromo-3-methylphenyl)oxazole

A mixture of compound A (12 g, 56 mmol) and vinylene carbonate (6.5 g, 75.5 mmol) in 25 g of polyphosphoric acid was heated at 170° C. for 3 hours. The residue was then added to 700 mL of water and extracted with 3×250 mL of ethyl acetate. The combined organic extracts were washed once with water, dried and evaporated. The residue was chromatographed on 200 g of silica gel using dichloromethane to provide 6.7 g (50%) of compound B as a white solid.

C. 2-[4-Bromo-3-(bromomethyl)-phenyl]oxazole

A mixture of compound B (6.5 g, 27.3 mmol), N-bromosuccinimide (9.72 g, 54.6 mmol) and benzoyl peroxide (250 mg) in 250 mL of carbon tetrachloride was refluxed for 8 hours while illuminating the solution with a sun lamp. The mixture was then cooled and filtered. The filtrate was concentrated to provide 10 g of a light yellow solid which was used in the next step without any further purification.

D. 2-Bromo-5-(2-oxazolyl)benzaldehyde

To a solution of 7 g of crude compound C in 15 mL of anhydrous dimethylsulfoxide under argon, 5.5 g of anhydrous trimethylamine N-oxide (prepared as described in Soderquist et. al. Tet. Letters., 27, 3961(1986)) was added and the mixture was stirred at 55° C. for 6 hours. The mixture was then cooled, added to 150 mL of ice/water and extracted with 3×100 mL of ethyl acetate. The combined organic extracts were washed once with 100 mL of brine, dried and evaporated. The residue was chromatographed on 300 mL of silica gel using Hexanes/ethyl acetate 8:1 to afford 2.2 g (46% for two steps) of compound D as a white solid.

E. N-(3,4-Dimethyl-5-isoxazolyl)-2-formyl-N-[(2-methoxyethoxy)methyl]-4'-(2-oxazolyl)[1,1'-biphenyl]-2-sulfonamide To a solution of 2.3 g (6 mmol) of compound B from Example 1 and 0.3 g (0.26 mmol) of tetrakis(triphenylphosphine)palladium(O) in 40 mL of toluene under argon, 20 mL of 2M aqueous sodium carbonate was added followed by 1.0 g (6.28 mmol) of compound D in 20 mL of 95% ethanol. The mixture was refluxed for 2 hours, diluted with 100 mL of water and extracted with 3×50 mL of ethyl acetate. The combined organic extracts were washed once with 100 mL of brine, dried and evaporated. The residue was chromatographed on 200 mL of silica gel using Hexanes/ethyl acetate 1:1 to afford 1.69 g (55%) of compound E as a colorless gum.

F. N-(3,4-Dimethyl-5-isoxazolyl)-2'-formyl-4'-(2-oxazolyl)[1,1'-biphenyl]-2-sulfonamide To a solution of 1.68 g (3.28 mmol) of compound E in 30 mL of 95% ethanol, 30 mL of 6N aqueous hydrochloric acid was added and refluxed for 1 hour. The mixture was then concentrated and diluted with 250 mL of water and extracted with 3×150 mL of ethyl acetate. The combined organic extracts were then washed once with water, dried and evaporated to provide 1.46 g (90%) of compound F as a colorless gum.

G. 2'-(Aminomethyl)-N-(3,4-dimethyl-5isoxazolyl)-4'-(2-oxazolyl)[1,1'-biphenyl]-2-sulfonamide To a solution of 0.28 g (0.66 mmol) of compound F in 25 mL of methanol, 5 g of ammonium acetate and 1 g of 3 Å molecular sieves were added and stirred at room temperature for 1 hour. Sodium triacetoxyborohydride (0.42 g, 1.98 mmol) was added and the mixture was stirred for an additional 45 minutes. The solution was filtered, concentrated to 10 mL, diluted with 25 mL of water and extracted with 3×25 mL of ethyl acetate. The combined organic extracts were then washed once with water, dried and evaporated. The residue was chromatographed on 15 g of silica gel using 5% methanol in dichloromethane to afford 0.1 g (36%) of compound G as a white solid.

H. N-(3,4-Dimethyl-5-isoxazolyl)-2'-[[(formylamino)methyl]-4'-(2-oxazolyl)[1,1'-biphenyl]-2-sulfonamide To a solution of 0.06 g (0.14 mmol) of compound G in 10 mL of dichloromethane at 0° C., 0.02 g of acetic formic anhydride and 0.02 g triethylamine were added. The mixture was slowly warmed to room temperature and stirred for 1 hour. The mixture was diluted with 10 mL of dichloromethane, washed with 20 mL of 0.1N aqueous hydrochloric acid and then with 20 mL of water. The organic layer was dried and evaporated. The residue was purified by reverse phase preparative HPLC on a 30×500 mm ODS S10 column using 56% solvent B (90% methanol, 10% water, 0.1% trifluroacetic acid) and 44% solvent A (10% methanol, 90% water, 0.1% trifluoroacetic acid). The appropriate fractions were collected, neutralized with aqueous sodium bicarbonate to pH 7 and concentrated to 10 mL. The solution was then acidified to pH 4 using dilute hydrochloric acid, and the white solid was filtered and dried to provide 0.013 g (21%) of the title compound.

M.p. 105°–109° C.

$^1$HNMR(CDCl$_3$): δ1.87 (s, 3H), 2.12 (s, 3H) 3.89 (ABq, J=4.1, 15.8 Hz, 1H), 4.50 (ABq, J=7.6, 15.8 Hz, 1H), 6.63 (br s, 1H), 7.03–7.93 (m, 10H), 8.14 (s, 1H).

$^{13}$C NMR (CDCl$_3$): δ6.83, 10.90, 39.80, 108.68, 124.26, 124.95, 127.29, 128.18, 128.79, 129.77, 130.26, 130.26, 130.52, 132.19, 133.58, 137.44, 137.61, 138.42, 138.88, 139.58, 154.37, 161.53, 162.25.

EXAMPLE 22

N-(3,4-Dimethyl-5-isoxazolyl)-2'-[[(methoxycarbonyl)amino]methyl]-4'-(2-oxazolyl)[1,1'-biphenyl]-2-sulfonamide

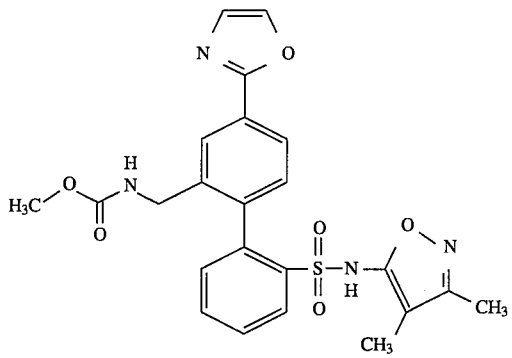

A. N-(3,4-Dimethyl-5-isoxazolyl)-2'-[[(methoxycarbonyl)amino]methyl]-4'-(2-oxazolyl)[1,1'-biphenyl]-2-sulfonamide To compound G from Example 21 (75 mg, 0.18 mmol) in 3.5 mL tetrahydrofuran, triethylamine (35 mg, 0.35 mmol) was added, followed by methyl chloroformate (17 mg, 0.18 mmol). The reaction was stirred at room temperature for 1 hour. Additional triethylamine (18 mg, 0.18 mmol) and methyl chloroformate (17 mg, 0.18 mmol) were added and the reaction was stirred at 40° C. for another 1.5 hours. The reaction mixture was concentrated and the residue was purified by preparative HPLC on a 3×500 mm ODS S10 column using 42% solvent A (10% methanol, 90% water, 0.1% trifluoroacetic acid) and 58% solvent B (90% methanol, 10% water, 0.1% trifluoroacetic acid) to provide the title compound (30 mg, 35%) as a white solid.

M.p. 110°–120° C.(amorphous).

Analysis calculated for C$_{23}$H$_{22}$N$_4$O$_6$S . 0.41H$_2$O: Calculated: C, 56.39; H, 4.69; N, 11.44; S, 6.54; Found: C, 56.11; H, 4.48; N, 11.19; S, 6.49.

EXAMPLE 23

N-[[2'-[[3,4-Dimethyl-5-isoxazolyl)amino]sulfonyl]-4-(2-oxazolyl)[1,1'-biphenyl]-2-yl]methyl]N'-methylurea

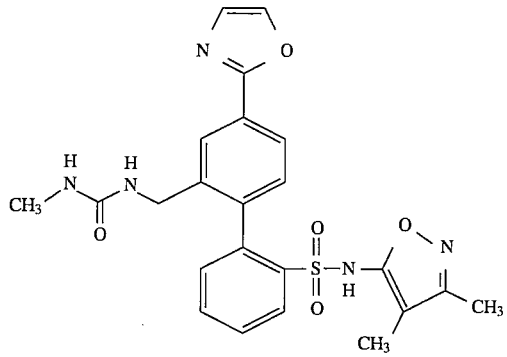

A. N-[[2'-[[3,4-Dimethyl-5-isoxazolyl)amino]sulfonyl]-4-(2-oxazolyl)[1,1'-biphenyl]-2-yl]methyl]N'-methylurea To compound G from Example 21 (75 mg, 0.18 mmol) in 7.1 mL tetrahydrofuran, methyl isocyanate (71 mg, 1.24 mmol) was added. The reaction was stirred at room temperature overnight and concentrated. The residue was purified by preparative HPLC on a 30×500 mm ODS S10 column using 46% solvent A (10% methanol, 90% water, 0.1% trifluoroacetic acid) and 54% solvent B (90% methanol, 10% water, 0.1% trifluoroacetic acid) to provide the title compound (38 mg, 45%) as a white solid.

M.p. >150° C., dec.

Analysis calculated for C$_{23}$H$_{23}$N$_5$O$_5$S . 0.45H$_2$O 0.2CH$_2$Cl$_2$: Calculated: C, 55.00; H, 4.83; N, 13.82; S, 6.33; Found: C, 54.57; H, 4.58; N, 13.61; S, 5.95.

EXAMPLE 24

N-(3,4-Dimethyl-5-isoxazolyl)-2'[[(methylsulfonyl)amino]methyl]-4'-(2-oxazolyl)-1,1'-biphenyl]-2-sulfonamide

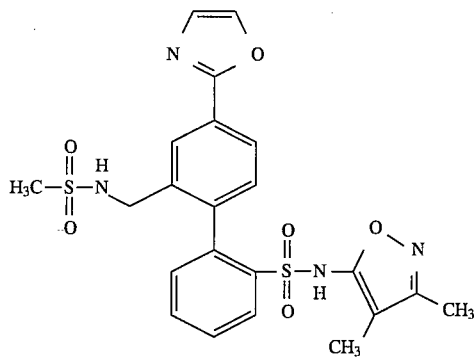

A. N-(3,4-Dimethyl-5-isoxazolyl)2'[[(methylsulfonyl)amino]methyl]-4'-(2-oxazolyl)1,1'-biphenyl]-2-sulfonamide To compound G from Example 21 (75 mg, 0.18 mmol) and triethylamine (54 mg, 0.53 mmol) in 7.1 ml tetrahydrofuran, methanesulfonyl chloride (57 mg, 0.5 mmol) was added. The reaction was stirred at 45° C. for 2 hours. The reaction mixture was concentrated and the pH of the solution was adjusted to 8 using sodium bicarbonate solution. It was then acidified to pH 5 with glacial acetic acid. The mixture was extracted with dichloromethane. The organic liquid was concentrated and the residue was purified by preparative HPLC on a 30×500 mm ODS S10 column using 47% solvent A (10% methanol, 90% water, 0.1% trifluoroacetic acid) and 53% solvent B (90% methanol, 10% water, 0.1% trifluoroacetic acid) to provide the title compound (27 mg, 30%) as a white solid.

M.p. 110°–120° C.(amorphous).

Analysis calculated for $C_{22}H_{22}N_4O_6S_2 \cdot 0.14CH_3COOH$: Calculated: C, 52.37; H, 4.45; N, 10.96; S, 12.56; Found: C, 52.43; H, 4.37; N, 10.76; S, 12.11.

EXAMPLE 25

N-[[2'-[[(3,4-Dimethyl-5-isoxazolyl)amino]sulfonyl]-4-(2-oxazolyl)[1,1'-biphenyl]-2-yl]methyl]acetamide

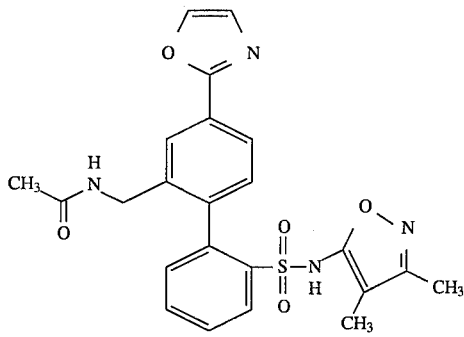

A. N-[[2'-[[(3,4-Dimethyl-5-isoxazolyl)amino]sulfonyl]-4-(2-oxazolyl)[1,1'-biphenyl]-2-yl]methyl]acetamide To a solution of 0.075 g (0.177 mmol) of compound G from Example 21 in 10 mL of dichloromethane at 0° C., 0.019 g (0.19 mmol) of acetic anhydride and 0.019 g triethylamine were added. The mixture was then slowly warmed to room temperature and stirred for 1 hour. The mixture was diluted with 10 mL of dichloromethane and washed with 20 mL of 0.1N aqueous hydrochloric acid and then with 20 mL of water. The organic layer was dried and evaporated. The residue was purified by reverse phase preparative HPLC on a 30×500 mm ODS S10 column using 58% solvent B (90% methanol, 10% water, 0.1% trifluoroacetic acid) and 42% solvent A (10% methanol, 90% water, 0.1% trifluoroacetic acid). The appropriate fractions were collected and neutralized with aqueous sodium bicarbonate to pH 7 and concentrated to 10 mL. The solution was acidified no pH 4 using dilute hydrochloric acid, and the white solid was filtered and dried to provide 0.041 g (50%) of the title compound.

M.p. 105°–107° C.

Analysis calculated for $C_{23}H_{22}N_4O_5S \cdot 0.42H_2O$: Calculated: C,58.27; H,4.86; N,11.82; S,6.76; Found: C,58.38; H,4.71; N,11.71; S,6.93.

EXAMPLE 26

N-[[2'-[[3,4-Dimethyl-5-isoxazolyl)amino]sulfonyl]-4-(2-oxazolyl)[1,1'-biphenyl]-2-yl]N'-phenylurea

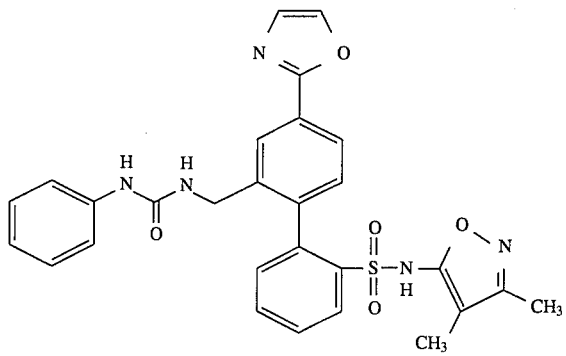

A. N-[[2'-[[3,4-Dimethyl-5-isoxazolyl)amino]sulfonyl]-4-(2-oxazolyl)[1,1'biphenyl]-2-yl]methyl]N'-phenylurea To compound G from Example 21 (25 mg, 0.059 mmol) in 3 mL tetrahydrofuran, phenyl isocyanate(56 mg, 0.47 mmol) was added. The reaction was stirred at room temperature overnight and concentrated. The residue was purified by preparative HPLC on a 30×500 mm ODS S10 column using 33% solvent A (10% methanol, 90% water, 0.1% trifluoroacetic acid) and solvent B (90% methanol, 10% water, 0.1% trifluoroacetic acid) to provide the title compound (18 mg, 56%) as a white solid.

$^1$HNMR(CDCl$_3$): δ1.82 (s, 3H), 2.16 (s, 3H), 3.99–4.38 (m, 2H), 6.06 (s, br, 1H), 6.91–8.03 (m, 15H).

$^{13}$C NMR (CDCl$_3$): δ7.60, 11.81, 42.65, 109.39, 119.92, 123.29, 124.13, 127.10, 128.26, 129.61, 130.68, 130.79, 132.96, 134.80, 137.72, 139.56, 140.00, 140.25, 140.43, 155.63, 156.58.

EXAMPLE 27

N-[[2'-[[3,4-Dimethyl-5-isoxazolyl)amino]sulfonyl]-4-(2-oxazolyl)[1,1'-biphenyl]-2-yl]N'-propylurea

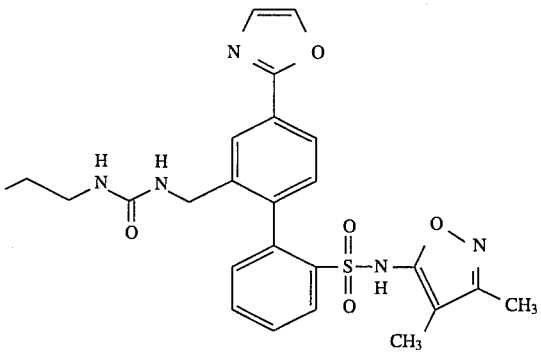

A. N-[[2'-[[3,4-Dimethyl-5-isoxazolyl)amino]sulfonyl]-4-(2-oxazolyl)[1,1'-biphenyl]-2-yl]methyl]N'-propylurea To compound G from Example 21 (20 mg, 0.047 mmol) in 3 mL tetrahydrofuran, propyl isocyanate (36 mg, 0.424 mmol) was added. The reaction mixture was stirred at room temperature overnight and concentrated. The residue was chromatographed on silica gel using 100:4.5 dichloromethane/methanol to provide the title compound (16 mg, 67%) as a light yellow solid.

¹H NMR (CD₃OD): δ0.89 (t, J=7 Hz, 3H), 1.46 (m, 2H), 1.70 (s, 3H), 2.10 (s, 3H), 3.06 (t, J=7 Hz, 2H), 4.08 (s, 2H), 7.10–8.12 (m, 9H).

¹³C NMR (CD₃OD): δ6.57, 10.58, 11.62, 24.37, 42.91, 124.83, 125.06, 127.97, 129.10, 129.62, 130.34, 131.67, 133.11, 133.74, 139.83, 140.44, 140.87, 141.24, 141.96, 160.91, 162.99, 163.42.

EXAMPLE 28

N-[[2'-[[(3,4-Dimethyl-5-isoxazolyl)amino]sulfonyl]-4-(2-oxazolyl)[1,1'-biphenyl]-2-yl]methyl]-N-methylacetamide

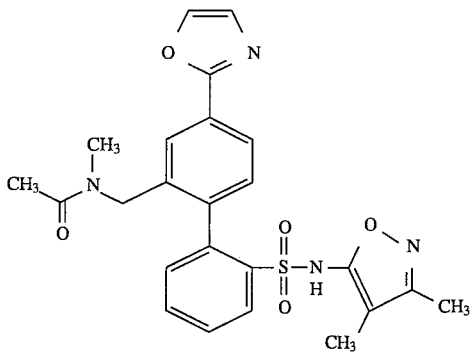

A. N-[[2'-[[(3,4-Dimethyl-5-isoxazolyl)amino]sulfonyl]-4-(2-oxazolyl)[1,1'-biphenyl]-2-yl]methyl]-N-methylacetamide To a solution of 0.15 g (0.35 mmol) of compound F from Example 21 in 15 mL of dichloromethane, methyl amine (33% solution in absolute ethanol, 0.13 mL, 1.06 mmol), glacial acetic acid (0.12 g, 2 mmol) and 1 g of 3 Å molecular sieves were added. The mixture was stirred at room temperature for 1 hour. Sodium triacetoxyborohydride (0.22 g, 1.06 mmol) was added and the mixture was stirred overnight. The solution was then filtered, washed once with water, dried and evaporated. The residue thus obtained was dissolved in 10 mL of dichloromethane, and 0.072 g (0.70 mmol) of acetic anhydride and 0.071 g (0.70 mmol) of triethylamine were added. The mixture was stirred at room temperature for 16 hours and evaporated. The residue was purified by reverse phase preparative HPLC on a 30×500 mm ODS S10 column using 58% solvent B (90% methanol, 10% water, 0.1% trifluoroacetic acid) and 42% solvent A (10% methanol, 90% water, 0.1% trifluoroacetic acid). The appropriate fractions were collected, neutralized with aqueous sodium bicarbonate to pH 7 and concentrated to 10 mL. The solution was acidified to pH 4 using glacial acetic acid and the white solid was filtered and dried to provide 0.069 g (41%) of the title compound as a light yellow solid.

M.p. 105°–115° C.

EXAMPLE 29

N-[[2'-[[(3,4-Dimethyl-5-isoxazolyl)amino]sulfonyl]-4-(2-oxazolyl)[1,1'-biphenyl]-2-yl]methyl]benzamide

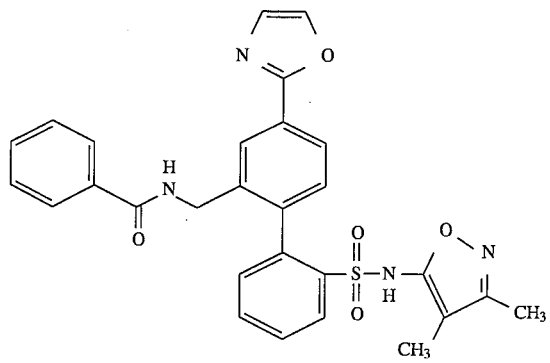

A. N-[[2'-[[(3,4-Dimethyl-5-isoxazolyl)amino]sulfonyl]-4-(2-oxazolyl)[1,1'-biphenyl]2-yl]methyl]benzamide To compound G from Example 21 (70 mg, 0.17 mmol) and benzoyl chloride (23 mg, 0.17 mmol) in 3.3 mL dichloromethane, triethylamine (37 mg, 0.36 mmol) was added. The reaction was stirred at room temperature for 1.5 hours and concentrated. The residue was purified by preparative HPLC on a 30×500 mm ODS S10 column using 33% solvent A (10% methanol, 90% water, 0.1% trifluoroacetic acid) and 67% solvent B (90% methanol, 10% water, 0.1% trifluoroacetic acid) to provide the title compound (30 mg, 34%) as a white solid.

M.p. 128°–135° C.(amorphous)

¹H NMR (CDCl₃): δ1.91 (s, 3H), 2.18 (s, 3H), 4.16–4.76 (m, 2H), 7.13–8.13 (m, 14H).

EXAMPLE 30

N-[[2'-[[(3,4,-Dimethyl-5-isoxazolyl)amino]sulfonyl]-4-(2-oxazolyl)-[1,1'-biphenyl]-2-yl]methyl]-2,2-dimethylpropanamide

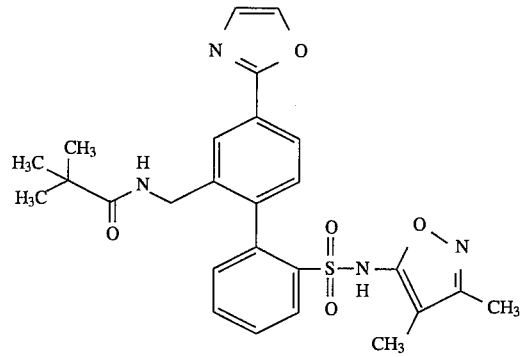

A. N-[[2'-[[(3,4-Dimethyl-5-isoxazolyl)amino]sulfonyl]-4-(2-oxazolyl)-[1,1'-biphenyl]-2-yl]methyl]-2,2-dimethylpropanamide To compound G from Example 21 (105 mg, 0.25 mmol) and trimethylacetyl chloride (30 mg, 0.25 mmol) in 4.9 mL dichloromethane, triethylamine (55 mg, 0.54 mmol) was added. The reaction was stirred at room temperature overnight and concentrated. The residue was purified by preparative HPLC on a 30×500 mm ODS S10 column using 33% solvent A (10% methanol, 90% water, 0.1% trifluoroacetic acid) and solvent B (90% methanol, 10% water, 0.1% trifluoroacetic acid) to provide the title compound (52 mg, 34%) as a white solid.

M.p. 122°–128° C.

$^1$H NMR (CDCl$_3$): δ1.18 (s, 9H), 1.93 (s, 3H), 2.18 (s, 3H), 3.96–4.46 (m, 2H), 7.24–8.05 (m, 9H).

What is claimed is:

1. A compound of the formula

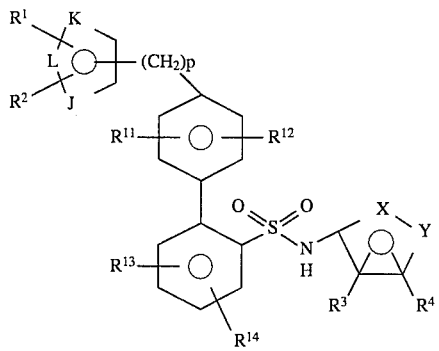

or an enantiomer, diastereomer or pharmaceutically acceptable salt thereof, wherein:

one of X and Y is N and the other is O;

$R^1$, $R^2$, $R^3$ and $R^4$ are each directly bonded to a ring carbon and are each independently
  (a) hydrogen;
  (b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with $Z^1$, $Z^2$ and $Z^3$;
  (c) halo;
  (d) hydroxyl;
  (e) cyano;
  (f) nitro;
  (g) —C(O)H or —C(O)R$^5$;
  (h) —CO$_2$H or —CO$_2$R$^5$;
  (i) —Z$^4$—NR$^6$R$^7$; or
  (j) —Z$^4$—N(R$^{10}$)—Z$^5$—NR$^8$R$^9$; or
  (k) R$^3$ and R$^4$ together may also be alkylene or alkenylene, either of which may be substituted with Z$^1$, Z$^2$ and Z$^3$, completing a 4- to 8-membered saturated, unsaturated or aromatic ring together with the carbon atoms to which they are attached;

R$^5$ is alkyl, alkenyl, alkynyl, cycloalkyl, cycloalkylalkyl, cycloalkenyl, cycloalkenylalkyl, aryl or aralkyl, any of which may be substituted with Z$^1$, Z$^2$ and Z$^3$;

R$^6$, R$^7$, R$^8$, R$^9$ and R$^{10}$ are each independently
  (a) hydrogen; or
  (b) alkyl, cycloalkyl, cycloalkylalkyl, cycloalkenylalkyl, aryl or aralkyl, any of which may be substituted with Z$^1$, Z$^2$ and Z$^3$; or R$^6$ and R$^7$ together may be alkylene or alkenylene, either of which may be substituted with Z$^1$, Z$^2$ and Z$^3$, completing a 3- to 8-membered saturated or unsaturated ring together with the nitrogen atom to which they are attached; or any two of R$^8$, R$^9$ and R$^{10}$ together are alkylene or alkenylene, either of which may be substituted with Z$^1$, Z$^2$ and Z$^3$, completing a 3- to 8-membered saturated or unsaturated ring together with the atoms to which they are attached;

R$^{11}$, R$^{12}$, R$^{13}$ and R$^{14}$ are each independently
  (a) hydrogen;
  (b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with Z$^1$, Z$^2$ and Z$^3$,
  (c) halo;
  (d) hydroxyl;
  (e) cyano;
  (f) nitro;
  (g) —C(O)H or —C(O)R$^5$;
  (h) —CO$_2$H or —CO$_2$R$^5$;
  (i) —SH, —S(O)$_n$R$^5$, —S(O)$_m$—OH, —S(O)$_m$—OR$^5$, —O—S(O)$_m$—OR$^5$, —O—S(O)$_m$OH or —O—S(O)$_m$—OR$^5$;
  (j) —Z$^4$—NR$^6$R$^7$; or
  (k) —Z$^4$—N(R$^{10}$)—Z$^5$—NR$^8$R$^9$;

Z$^1$, Z$^2$ and Z$^3$ are each independently
  (a) hydrogen;
  (b) halo;
  (c) hydroxy;
  (d) alkyl;
  (e) alkenyl;
  (f) aralkyl;
  (g) alkoxy;
  (h) aryloxy;
  (i) aralkoxy;
  —SH, —S(O)$_n$Z$^6$, —S(O)$_m$—OH, —S(O)$_m$—OZ$^6$, —O—S(O)$_m$—Z$^6$, —O—S(O)$_m$OH or —O—S(O)$_m$—OZ$^6$;
  (k) oxo;
  (l) nitro;
  (m) cyano;
  (n) —C(O)H or —C(O)Z$^6$;
  (o) —CO$_2$H or —CO$_2$Z$^6$;
  (p) —Z$^4$—NZ$^7$Z$^8$;
  (q) —Z$^4$—N(Z$^{11}$)—Z$^5$—H;
  (r) —Z$^4$—N(Z$^{11}$)—Z$^5$—Z$^6$; or
  (s) —Z$^4$—N(Z$^{11}$)—Z$^5$—NZ$^7$Z$^8$;

Z$^4$ and Z$^5$ are each independently
  (a) a single bond;
  (b) —Z$^9$—S(O)$_n$—Z$^{10}$—;
  (c) —Z$^9$—C(O)—Z$^{10}$—;
  (d) —Z$^9$—C(S)—Z$^{10}$—;
  (e) —Z$^9$—O—Z$^{10}$—;
  (f) —Z$^9$—S—Z$^{10}$—;
  (g) —Z$^9$—O—C(O)—Z$^{10}$—; or
  (h) —Z$^9$—C(O)—O—Z$^{10}$—;

Z$^6$ is alkyl, alkenyl, alkynyl, cycloalkyl, cycloalkylalkyl, cycloalkenyl, cycloalkenylalkyl, aryl or aralkyl;

Z$^7$ and Z$^8$ are each independently hydrogen, alkyl, cycloalkyl, cycloalkylalkyl, cycloalkenylalkyl, aryl or aralkyl or Z$^7$ and Z$^8$ together are alkylene or alkenylene, completing a 3- to 8-membered saturated or unsaturated ring together with the nitrogen atom to which they are attached;

Z$^9$ and Z$^{10}$ are each independently a single bond, alkylene, alkenylene or alkynylene;

Z$^{11}$ is
  (a) hydrogen; or
  (b) alkyl, cycloalkyl, cycloalkylalkyl, cycloalkenylalkyl, aryl or aralkyl;

or any two of Z$^7$, Z$^8$ and Z$^{11}$ together are alkylene or alkenylene, completing a 3- to 8-membered saturated or unsaturated ring together with the atoms to which they are attached;

J is O, S, N or NR$^{15}$;

K and L are N or C, provided that at least one of K or L is C;

R$^{15}$ is hydrogen, alkyl, hydroxyethoxy methyl or methoxyethoxy methyl;

each m is independently 1 or 2;

each n is independently 0, 1 or 2; and p is 0 or an integer from 1 to 2.

2. A compound of claim 1, wherein $R^1$ and $R^2$ are each independently hydrogen, alkyl, alkoxy, aryl, hydroxyalkyl, —$CO_2R^5$ or —$Z^4$—$NR^6R^7$.

3. A compound of claim 1, wherein $R^3$ and $R^4$ are each independently alkyl.

4. A compound of claim 1, wherein $R^{11}$ and $R^{12}$ are each independently hydrogen, hydroxy, amino or substituted lower alkyl.

5. A compound of claim 1, wherein $R^1$ and $R^2$ are each independently hydrogen, alkyl, alkoxy, aryl, hydroxyalkyl, —$CO_2R^5$ or —$Z^4$—$NR^6R^7$; $R^3$ and $R^4$ are each independently alkyl; and $R^{11}$ and $R^{12}$ are each independently hydrogen, hydroxy, amino or substituted lower alkyl.

6. A compound of claim 1, wherein $R^1$ and $R^2$ are each independently hydrogen or lower alkyl.

7. A compound of claim 1, wherein $R^3$ and $R^4$ are each independently alkyl of 1 to 4 carbon atoms.

8. A compound of claim 1, wherein $R^3$ and $R^4$ are each methyl.

9. A compound of claim 1, wherein $R^{11}$ and $R^{12}$ are each independently hydrogen, hydroxy or substituted lower alkyl.

10. A compound of claim 1, wherein $R^1$ and $R^2$ are each independently hydrogen or lower alkyl; $R^3$ and $R^4$ are each independently alkyl of 1 to 4 carbon atoms; and $R^{11}$ and $R^{12}$ are each independently hydrogen, hydroxy or substituted lower alkyl.

11. A compound of claim 1, wherein $R^1$ and $R^2$ are each independently hydrogen or lower alkyl; $R^3$ and $R^4$ are each methyl; and $R^{11}$ and $R^{12}$ are each independently hydrogen, hydroxy or substituted lower alkyl.

12. A compound of claim 1, wherein p is 0.

13. A compound of claim 1, wherein p is 1.

14. A compound of claim 1, wherein p is 0; $R^1$ and $R^2$ are each independently hydrogen or lower alkyl; $R^3$ and $R^4$ are each methyl; and $R^{11}$ and $R^{12}$ are each indepenently hydrogen, hydroxy or substituted lower alkyl.

15. A compound of claim 1, wherein p is 1; $R^1$ and $R^2$ are each independently hydrogen or lower alkyl; $R^3$ and $R^4$ are each methyl; and $R^{11}$ and $R^{12}$ are each independently hydrogen, hydroxy or substituted lower alkyl.

16. A compound of claim 1, selected from the group consisting of:

N-(3,4-Dimethyl-5-isoxazolyl)-4'-(2-oxazolyl)[1,1'-biphenyl]-2-sulfonamide;

N-(3,4-Dimethyl-5-isoxazolyl)-4'-(2-thiazolyl)[1,1'-biphenyl]-2-sulfonamide;

N-(3,4-Dimethyl-5-isoxazolyl)-4'-(4,5-dimethyl-2-oxazolyl)[1,1'-biphenyl]-2-sulfonamide;

N-(3,4-Dimethyl-5-isoxazolyl)-4'-(5-oxazolyl)[1,1'-biphenyl]-2-sulfonamide;

N-(3,4 -Dimethyl-5-isoxazolyl)-4'-(4-oxazolyl)[1,1'-biphenyl]-2-sulfonamide;

N-(3,4-Dimethyl-5-isoxazolyl)-4'-(2-methyl-4-oxazolyl)[1,1'-biphenyl]-2-sulfonamide;

N-(3,4-Dimethyl-5-isoxazolyl)-4'-(4-methyl-2-oxazolyl)[1,1'-biphenyl]-2-sulfonamide;

N-(3,4-Dimethyl-5-isoxazolyl)-4'-(5-methyl-2-oxazolyl)[1,1'-biphenyl]-2-sulfonamide;

N-(3,4-Dimethyl-5-isoxazolyl)-4'-(1H-pyrazol-1-yl)[1,1'-biphenyl]-2-sulfonamide;

N-(3,4-Dimethyl-5-isoxazolyl)-4'-[1-[(2-methoxyethoxy)methyl]-1H-imidazol-2-yl][1,1'-biphenyl]-2-sulfonamide;

N-(3,4-Dimethyl-5-isoxazolyl)-4'-[1-[(2-hydroxyethoxy)methyl]-1H-imidazol-2-yl][1,1'-biphenyl]-2-sulfonamide;

N-(3,4-Dimethyl-5-isoxazolyl)-4'-(1-methyl-1H-imidazol-2-yl)[1,1'-biphenyl]-2-sulfonamide;

N-(3,4-Dimethyl-5-isoxazolyl)-4'-(1H-imidazol-2-yl)[1,1'-biphenyl]-2-sulfonamide;

N-(3,4-Dimethyl-5-isoxazolyl)-4'-(5-methyl-4-oxazolyl)[1,1'-biphenyl]-2-sulfonamide;

N-(3,4-Dimethyl-5-isoxazolyl)-4'-(1H-imidazol-1-ylmethyl)[1,1'-biphenyl]-2-sulfonamide;

N-(3,4-Dimethyl-5-isoxazolyl)-4'-(3-isoxazolyl)[1,1'-biphenyl]-2-sulfonamide;

N-(3,4-Dimethyl-5-isoxazolyl)-4'-(2-oxazolylmethyl)[1,1'-biphenyl]-2-sulfonamide;

N-(3,4-Dimethyl-5-isoxazolyl)-4'-(5-isoxazolyl)[1,1'-biphenyl]-2-sulfonamide;

N-(3,4-Dimethyl-5-isoxazolyl)-2'-hydroxy-4'-(2-oxazolyl)[1,1'-biphenyl]-2-sulfonamide;

2-[2'-[[(3,4-Dimethyl-5-isoxazoly)amino]sulfonyl][1,1'-biphenyl]-4-yl]-4-oxazolecarboxamide;

N-(3,4-Dimethyl-5-isoxazolyl) -2'-[(formylamino)methyl]-4'-(2-oxazolyl)[1,1'-biphenyl]-2-sulfonamide;

2'-(Aminomethyl)-N-(3,4-dimethyl-5-isoxazolyl)-4'-(2-oxazolyl)[1,1'-biphenyl]-2-sulfonamide;

N-(3,4-Dimethyl-5-isoxazolyl)-2'-[[(methoxycarbonyl)amino]methyl]-4'-(2-oxazolyl)[1,1'-biphenyl]-2-sulfonamide;

N-[[2'-[[3,4-Dimethyl-5-isoxazolyl)amino]sulfonyl]-4-(2-oxazolyl)[1,1'-biphenyl]-2-yl]methyl]N'-methylurea;

N-(3,4-Dimethyl-5-isoxazolyl)-2'[[(methylsulfonyl)amino]methyl]-4'-(2-oxazolyl)-1,1'-biphenyl]-2-sulfonamide;

N-[[2'-[[(3,4-Dimethyl-5-isoxazolyl)amino]sulfonyl]-4-(2-oxazolyl)[1,1'-biphenyl]-2-yl]methyl]acetamide;

N-[[2'-[[3,4-Dimethyl-5-isoxazolyl)amino]sulfonyl]-4-(2-oxazolyl)[1,1'-biphenyl]-2-yl]methyl]N'-phenylurea;

N-[[2'-[[3,4-Dimethyl-5-isoxazolyl)amino]sulfonyl]-4-(2-oxazolyl)[1,1'-biphenyl]-2-yl]methyl]N'-propylurea;

N-[[2'-[[(3,4-Dimethyl-5-isoxazolyl)amino]sulfonyl]-4-(2-oxazolyl)[1,1'-biphenyl]-2-yl]methyl]-N-methylacetamide;

N-[[2'-[[(3,4-Dimethyl-5-isoxazolyl)amino]sulfonyl]-4-(2-oxazolyl)[1,1'-biphenyl]-2-yl]methyl]benzamide; and N-[[2'-[[(3,4-Dimethyl-5-isoxazolyl)amino]sulfonyl]-4-(2-oxazolyl)[1,1'-biphenyl]-2-yl]-methyl]-2,2-dimethylpropanamide.

17. A compound of claim 1, selected from the group consisting of:

N-(3,4-Dimethyl-5-isoxazolyl)-4'-(2-oxazolyl)[1,1'-biphenyl]-2-sulfonamide;

N-(3,4-Dimethyl-5-isoxazolyl)-4'-(2-thiazolyl)[1,1'-biphenyl]-2-sulfonamide;

N-(3,4-Dimethyl-5-isoxazolyl)-4'-(5-oxazolyl)[1,1'-biphenyl]-2-sulfonamide;

N-(3,4-Dimethyl-5-isoxazolyl)-4'-(4-oxazolyl)[1,1'-biphenyl]-2-sulfonamide;

N-(3,4-Dimethyl-5-isoxazolyl)-4'-(1H-pyrazol-1-yl)[1,1'-biphenyl]-2-sulfonamide;

N-(3,4-Dimethyl-5-isoxazolyl)-4'-(1-methyl-1H-imidazol-2-yl)[1,1'-biphenyl]-2-sulfonamide;

N-(3,4-Dimethyl-5-isoxazolyl)-2'-hydroxy-4'-(2-oxazolyl)[1,1'-biphenyl]-2-sulfonamide;

2-[2'-[[(3,4-Dimethyl-5-isoxazoly)amino]sulfonyl][1,1'-biphenyl]-4-yl]-4-oxazolecarboxamide;

N-(3,4-Dimethyl-5-isoxazolyl)-2'-[(formylamino)methyl]-4'-(2-oxazolyl)[1,1'-biphenyl]-2-sulfonamide;

N-(3,4-Dimethyl-5-isoxazolyl)-2'-[[(methoxycarbonyl)amino]methyl]-4'-(2-oxazolyl)[1,1'-biphenyl]-2-sulfonamide;

N-[[2'-[[3,4-Dimethyl-5-isoxazolyl)amino]sulfonyl]-4-(2-oxazolyl)[1,1'-biphenyl]-2-yl]methyl]N'-methylurea;

N-(3,4-Dimethyl-5-isoxazolyl)-2'[[(methylsulfonyl)amino]methyl]-4'-(2-oxazolyl)-1,1'-biphenyl]-2-sulfonamide;

N-[[2-[[(3,4-Dimethyl-5-isoxazolyl)amino]sulfonyl]-4-(2-oxazolyl)[1,1'-biphenyl]-2-yl]methyl]acetamide;

N-[[2-[[3,4-Dimethyl-5-isoxazolyl)amino]sulfonyl]-4-(2-oxazolyl)[1,1'-biphenyl]-2-yl]methyl]N'-phenylurea;

N-[[2-[[3,4-Dimethyl-5-isoxazolyl)amino]sulfonyl]-4-(2-oxazolyl)[1,1'-biphenyl]-2-yl]methyl]N'-propylurea;

N-[[2-[[(3,4-Dimethyl-5-isoxazolyl)amino]sulfonyl]-4-(2-oxazolyl)[1,1'-biphenyl]-2-yl]methyl]-N-methylacetamide;

N-[[2-[[(3,4-Dimethyl-5-isoxazolyl)amino]sulfonyl]-4-(2-oxazolyl)[1,1'-biphenyl]-2-yl]methyl]benzamide; and N-[[2-[[(3,4-Dimethyl-5-isoxazolyl)amino]sulfonyl]-4-(2-oxazolyl)[1,1'-biphenyl]-2-yl]methyl]-2,2-dimethylpropanamide.

18. A method of treating endothelin-related disorders in a mammal, which comprises administering to said mammal an effective endothelin-related disorder treating amount of a compound of claim 1.

19. A method of treating hypertension, which comprises administering an effective hypertension treating amount of a compound of claim 1.

20. A method of treating pulmonary hypertension, which comprises administering an effective pulmonary hypertension treating amount of a compound of claim 1.

21. A method of treating renal, glomerular or mesangial cell disorders, which comprises administering an effective renal, glomerular or mesangial cell disorder treating amount of a compound of claim 1.

22. A method of treating endotoxemia, which comprises administering an effective endotoxemia treating amount of a compound of claim 1.

23. A method of treating ischemia, which comprises administering an effective ischemia treating amount of a compound of claim 1.

24. A method of inhibiting cell growth, which comprises administering an effective cell growth inhibiting amount of a compound of claim 1.

25. A method of treating atherosclerosis, which comprises administering an effective atherosclerosis treating amount of a compound of claim 1.

26. A method of treating restenosis, which comprises administering an effective restenosis treating amount of a compound of claim 1.

27. A method of treating subarachnoid hemorrhage, which comprises administering an effective subarachnoid hemorrhage treating amount of a compound of claim 1.

28. A method of treating benign prostatic hypertrophy, which comprises administering a begign prostatic hypertrophy treating amount of a compound of claim 1.

29. A compound of the formula

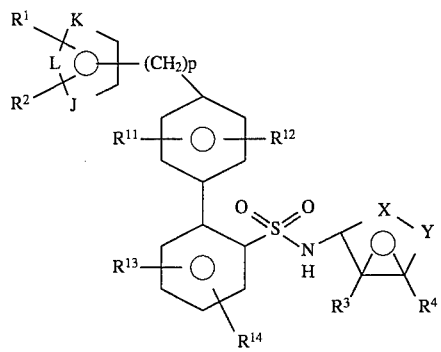

or an enantiomer, diastereomer or pharmaceutically acceptable salt thereof, wherein:

one of X and Y is N and the other is O; $R^1$, $R^2$, $R^3$ and $R^4$ are each directly bonded to a ring carbon and are each independently
(a) hydrogen;
(b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with $Z^1$, $Z^2$ and $Z^3$;
(c) halo;
(d) hydroxyl;
(e) cyano;
(f) nitro;
(g) —C(O)H or —C(O)$R^5$;
(h) —CO$_2$H or —CO$_2R^5$;
(i) —$Z^4$—NR$^6$R$^7$; or
(j) —$Z^4$—N(R$^{10}$)—$Z^5$—NR$^8$R$^9$; or
(k) $R^3$ and $R^4$ together may also be alkylene or alkenylene, either of which may be substituted with $Z^1$, $Z^2$ and $Z^3$, completing a 4- to 8-membered saturated, unsaturated or aromatic ring together with the carbon atoms to which they are attached;

$R^5$ is alkyl, alkenyl, alkynyl, cycloalkyl, cycloalkylalkyl, cycloalkenyl, cycloalkenylalkyl, aryl or aralkyl, any of which may be substituted with $Z^1$, $Z^2$ and $Z^3$;

$R^6$, $R^7$, $R^8$, $R^9$ and $R^{10}$ are each independently
(a) hydrogen; or
(b) alkyl, cycloalkyl, cycloalkylalkyl, cycloalkenylalkyl, aryl or aralkyl, any of which may be substituted with $Z^1$, $Z^2$ and $Z^3$; or $R^6$ and $R^7$ together may be alkylene or alkenylene, either of which may be substituted with $Z^1$, $Z^2$ and $Z^3$, completing a 3- to 8-membered saturated or unsaturated ring together with the nitrogen atom to which they are attached; or any two of $R^8$, $R^9$ and $R^{10}$ together are alkylene or alkenylene, either of which may be substituted with $Z^1$, $Z^2$ and $Z^3$, completing a 3- to 8-membered saturated or unsaturated ring together with the atoms to which they are attached;

$R^{11}$, $R^{12}$, $R^{13}$ and $R^{14}$ are each independently
(a) hydrogen;
(b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with $Z^1$, $Z^2$ and $Z^3$,
(c) halo;
(d) hydroxyl;
(e) cyano;
(f) nitro;
(g) —C(O)H or —C(O)$R^5$;

(h) —CO₂H or —CO₂R⁵;
(i) —SH, —S(O)ₙR⁵, —S(O)ₘ—OH, —S(O)ₘ—OR⁵, —O—S(O)ₘ—OR⁵, —O—S(O)ₘOH or —O—S(O)ₘ—OR⁵;
(j) —Z⁴—NR⁶R⁷; or
(k) —Z⁴—N(R¹⁰)—Z⁵-NR⁸R⁹;

Z¹ Z² and Z³ are each independently
(a) hydrogen;
(b) halo;
(c) hydroxy;
(d) alkyl;
(e) alkenyl;
(f) aralkyl;
(g) alkoxy;
(h) aryloxy;
(i) aralykoxy;
(j) —SH, —S(O)ₙZ⁶, —S(O)ₘ—OH,—S(O)ₘ—OZ⁶, —O—S(O)ₘ—Z⁶, —O—S(O)ₘOH or —O—S(O)ₘ—OZ⁶;
(k) oxo;
(l) nitro;
(m) cyano;
(n) —C(O)H or —C(O)Z⁶;
(o) —CO₂H or —CO₂Z⁶;
(p) —Z⁴NZ⁷Z⁸;
(q) —Z⁴—N(Z¹¹)—Z⁵—Z⁶; or
(r) —Z⁴—N(Z¹¹)—Z⁵—NZ⁷Z⁸;

Z⁴ and Z⁵ are each independently
(a) a single bond;
(b) —Z⁹—S(O)ₙ—Z¹⁰—;
(c) —Z⁹—C(O)—Z¹⁰—;
(d) —Z⁹—C(S)—Z¹⁰—;
(e) —Z⁹—O—Z¹⁰—;
(f) —Z⁹—S—Z¹⁰—; or
(g) —Z⁹—O—C(O)—Z¹⁰—;
(h) —Z⁹—C(O)—O—Z¹⁰—;

Z⁶ is alkyl, alkenyl, alkynyl, cycloalkyl, cycloalkylalkyl, cycloalkenyl, cycloalkenylalkyl, aryl or aralkyl;

Z⁷ and Z⁸ are each independently hydrogen, alkyl, cycloalkyl, cycloalkylalkyl, cycloalkenylalkyl, aryl or aralkyl or Z⁷ and Z⁸ together are alkylene or alkenylene, completing a 3- to 8-membered saturated or unsaturated ring together with the nitrogen atom to which they are attached;

Z⁹ and Z¹⁰ are each independently a single bond, alkylene, alkenylene or alkynylene;

Z¹¹ is
(a) hydrogen;
(b) alkyl, cycloalkyl, cycloalkylalkyl, cycloalkenylalkyl, aryl or aralkyl;

or any two of Z⁷, Z⁸ and Z¹¹ together are alkylene or alkenylene, completing a 3- to 8-membered saturated or unsaturated ring together with the atoms to which they are attached;

J is O, S, N or NR¹⁵;

K and L are N or C, provided that at least one of K or L is C;

R¹⁵ is hydrogen, alkyl, hydroxyethoxy methyl or methoxyethoxy methyl;

each m is independently 1 or 2;

each n is independently 0, 1 or 2; and p is 0 or an integer from 1 to 2.

30. A method of treating congestive heart failure, which comprises administering an effective congestive heart failure treating amount of a compound of claim 1.

31. A compound of claim 1, which is N-(3,4-Dimethyl-5-isoxazolyl)-4'-(2-oxazolyl)[1,1'-biphenyl]-2-sulfonamide, or a pharmaceutically acceptable salt thereof.

32. The compound of claim 31, which is N-(3,4-Dimethyl-5-isoxazolyl)4'-(2-oxazolyl)[1,1'-biphenyl]-2-sulfonamide.

33. The compound of claim 31, which is the sodium salt of N-(3,4-Dimethyl-5-isoxazolyl)-4'-(2-oxazolyl)[1,1'-biphenyl]-2-sulfonamide.

34. A method of treating congestive heart failure, which comprises administering an effective congestive heart failure treating amount of a compound of claim 31.

35. A compound of claim 1, which is N-(3,4-Dimethyl-5-isoxazolyl)-4'-(2-thiazolyl)[1,1'-biphenyl]-2-sulfonamide, or a pharmaceutically acceptable salt thereof.

36. The compound of claim 35, which is N-(3,4-Dimethyl-5-isoxazolyl)4'-(2-thiazolyl)[1,1'-biphenyl]-2-sulfonamide.

37. The compound of claim 35, which is the sodium salt of N-(3,4-Dimethyl-5-isoxazolyl)-4'-(2-thiazolyl)[1,1'-biphenyl]-2-sulfonamide.

38. A method of treating congestive heart failure, which comprises administering an effective congestive heart failure treating amount of a compound of claim 35.

39. A compound of claim 1, which is N-(3,4-Dimethyl-5-isoxazolyl)-4'-(5-oxazolyl)[1,1'-biphenyl]-2-sulfonamide, or a pharmaceutically acceptable salt thereof.

40. The compound of claim 39, which is N-(3,4-Dimethyl-5-isoxazolyl)4'-(5-oxazolyl)[1,1'-biphenyl]-2-sulfonamide.

41. The compound of claim 39, which is the sodium salt of N-(3,4-Dimethyl-5-isoxazolyl)-4'-(5-oxazolyl)[1,1'-biphenyl]-2- sulfonamide.

42. A method of treating congestive heart failure, which comprises administering an effective congestive heart failure treating amount of a compound of claim 39.

43. A compound of claim 1, which is N-(3,4-Dimethyl-5-isoxazolyl)-4'-(4-oxazolyl)[1,1'-biphenyl]-2-sulfonamide, or a pharmaceutically acceptable salt thereof.

44. The compound of claim 43, which is N-(3,4-Dimethyl-5-isoxazolyl)4'-(4-oxazolyl)[1,1'-biphenyl]-2-sulfonamide.

45. The compound of claim 43, which is the sodium salt of N-(3,4-Dimethyl-5-isoxazolyl)-4'-(4-oxazolyl)[1,1'-biphenyl]-2-sulfonamide.

46. A method of treating congestive heart failure, which comprises administering an effective congestive heart failure treating amount of a compound of claim 43.

47. A compound of claim 1, which is N-(3,4-Dimethyl-5-isoxazolyl)-4'-(4-methyl-2-oxazolyl)[1,1'-biphenyl]-2-sulfonamide, or a pharmaceutically acceptable salt thereof.

48. The compound of claim 47, which is N-(3,4-Dimethyl-5-isoxazolyl)4'-(4-methyl-2-oxazolyl)[1,1'-biphenyl]-2-sulfonamide.

49. The compound of claim 47, which is the sodium salt of N-(3,4-Dimethyl-5-isoxazolyl)-4'-(4-methyl-2-oxazolyl)[1,1'-biphenyl]-2-sulfonamide.

50. A method of treating congestive heart failure, which comprises administering an effective congestive heart failure treating amount of a compound of claim 47.

51. A compound of claim 1, which is N-(3,4-Dimethyl-5-isoxazolyl)-4'-(1-methyl-1H-imidazol-2-yl)[1,1'-biphenyl]-2-sulfonamide, or a pharmaceutically acceptable salt thereof.

52. The compound of claim 51, which is N-(3,4-Dimethyl-5-isoxazolyl)-4'-(1-methyl-1H-imidazol-2-yl )[1,1'-biphenyl]-2-sulfonamide.

53. The compound of claim 51, which is the sodium salt of N-(3,4-Dimethyl-5-isoxazolyl)-4'-(1-methyl-1H-imidazol-2-yl)[1,1'-biphenyl]-2-sulfonamide.

54. A method of treating congestive heart failure, which comprises administering an effective congestive heart failure treating amount of a compound of claim 51.

55. A compound of claim 1, which is N-(3,4-Dimethyl-5-isoxazolyl)-4'-(5-methyl-4-oxazolyl)[1,1'-biphenyl]-2-sulfonamide, or a pharmaceutically acceptable salt thereof.

56. The compound of claim 55, which is N-(3,4-Dimethyl-5-isoxazolyl)-4'-(5-methyl-4-oxazolyl)[1,1'-biphenyl]-2-sulfonamide.

57. The compound of claim 55, which is the sodium salt of N-(3,4-Dimethyl-5-isoxazolyl)-4'-(5-methyl-4-oxazolyl)[1,1'-biphenyl]-2-sulfonamide.

58. A method of treating congestive heart failure, which comprises administering an effective congestive heart failure treating amount of a compound of claim 55.

59. A compound of claim 1, which is N-(3,4-Dimethyl-5-isoxazolyl)-4'-(3-isoxazolyl)[1,1'-biphenyl]-2-sulfonamide, or a pharmaceutically acceptable salt thereof.

60. The compound of claim 59, which is N-(3,4-Dimethyl-5-isoxazolyl)-4'-(3-isoxazolyl)[1,1'-biphenyl]-2-sulfonamide.

61. The compound of claim 59, which is the sodium salt of N-(3,4-Dimethyl-5-isoxazolyl)-4'-(3-isoxazolyl)[1,1'-biphenyl]-2-sulfonamide.

62. A method of treating congestive heart failure, which comprises administering an effective congestive heart failure treating amount of a compound of claim 59.

63. A compound of claim 1, which is N-(3,4-Dimethyl-5-isoxazolyl)-4'-(2-oxazolyl-methyl)[1,1'-biphenyl]-2-sulfonamide, or a pharmaceutically acceptable salt thereof.

64. The compound of claim 63, which is N-(3,4-Dimethyl-5-isoxazolyl)-4'-(2-oxazolyl-methyl)[1,1'-biphenyl]-2-sulfonamide.

65. The compound of claim 63, which is the sodium salt of N-(3,4-Dimethyl-5-isoxazolyl)-4'-(2-oxazolyl-methyl)[1,1'-biphenyl]-2-sulfonamide.

66. A method of treating congestive heart failure, which comprises administering an effective congestive heart failure treating amount of a compound of claim 63.

67. A compound of claim 1, which is N-(3,4-Dimethyl-5-isoxazolyl)-2'-hydroxy-4'-(2-oxazolyl)[1,1'-biphenyl]-2-sulfonamide, or a pharmaceutically acceptable salt thereof.

68. The compound of claim 67, which is N-(3,4-Dimethyl-5-isoxazolyl)-2'-hydroxy-4'-(2-oxazolyl)[1,1'-biphenyl]-2-sulfonamide.

69. The compound of claim 67, which is the sodium salt of N-(3,4-Dimethyl-5-isoxazolyl)-2'-hydroxy-4'-(2-oxazolyl)[1,1'-biphenyl]-2-sulfonamide.

70. A method of treating congestive heart failure, which comprises administering an effective congestive heart failure treating amount of a compound of claim 67.

71. The method of claim 18, wherein said compound of claim 1 is used in combination with at least one angiotensin II (AII) receptor antagonist, renin inhibitor, angiotensin converting enzyme (ACE) inhibitor, or dual neutral endopeptidase (NEP)-ACE inhibitor.

72. A pharmaceutical composition for the treatment of an endothelin-related disorder, comprising a compound of claim 1 in an amount effective therefor and a physiologically acceptable vehicle or carrier.

73. A pharmaceutical composition of claim 72, further comprising at least one angiotensin II (AII) receptor antagonist, renin inhibitor, angiotensin converting enzyme (ACE) inhibitor, or dual neutral endopeptidase (NEP)-ACE inhibitor.

* * * * *